United States Patent [19]
Jones et al.

[11] Patent Number: 5,849,011
[45] Date of Patent: Dec. 15, 1998

[54] MEDICAL DEVICE WITH TRIGGER ACTUATION ASSEMBLY

[75] Inventors: Christopher Scott Jones, Palo Alto; Phillip R. Sommer, Newark; James Allen Baker, Jr., Palo Alto, all of Calif.

[73] Assignee: Vidamed, Inc., Fremont, Calif.

[21] Appl. No.: 588,452

[22] Filed: Jan. 18, 1996

Related U.S. Application Data

[63] Continuation-in-part of Ser. No. 492,272, Jun. 19, 1995.
[51] Int. Cl.[6] .................................................. A61B 17/39
[52] U.S. Cl. .............................. 606/47; 606/41; 606/46; 606/49
[58] Field of Search ........................................ 606/40–52

[56] References Cited

U.S. PATENT DOCUMENTS

| | | |
|---|---|---|
| 5,342,357 | 8/1994 | Nardella . |
| 5,360,428 | 11/1994 | Hutchinson, Jr. . |
| 5,366,490 | 11/1994 | Edwards . |
| 5,370,675 | 12/1994 | Edwards .................................. 607/101 |
| 5,385,544 | 1/1995 | Edwards . |
| 5,409,453 | 4/1995 | Lundquist . |
| 5,421,819 | 6/1995 | Edwards . |
| 5,435,805 | 7/1995 | Edwards . |

FOREIGN PATENT DOCUMENTS

WO93/15664  8/1993  WIPO .

*Primary Examiner*—David M. Shay
*Attorney, Agent, or Firm*—Flehr Hohbach Test Albritton & Herbert LLP

[57] ABSTRACT

An electrosurgical device for medical treatment of tissue at a treatment site through a body opening. The device includes a sheath having proximal and distal extremities and having a passageway extending from the proximal extremity to the distal extremity. A guide tube is slidably mounted in the passageway of the sheath and has proximal and distal extremities and a lumen extending from the proximal extremity to the distal extremity. A needle electrode is slidably mounted in the lumen of the guide tube and has proximal and distal extremities. Insulation is coaxially disposed on the needle electrode. A handle adapted to be gripped by the human hand is provided and the proximal extremity of the guide tube is mounted on the handle. An assembly is carried by the handle for bending the distal extremity of the guide tube at an angle with respect to the longitudinal axis. The needle electrode is adapted to be coupled to an energy source. A single actuation element is carried by the handle and coupled to the needle electrode and the insulation. The actuation element is movable in a single stroke from a first position in which the needle electrode and the insulation are disposed within the guide tube and a second position in which the needle electrode and the insulation are disposed in the tissue at the treatment site. A method for using the device is provided.

17 Claims, 15 Drawing Sheets

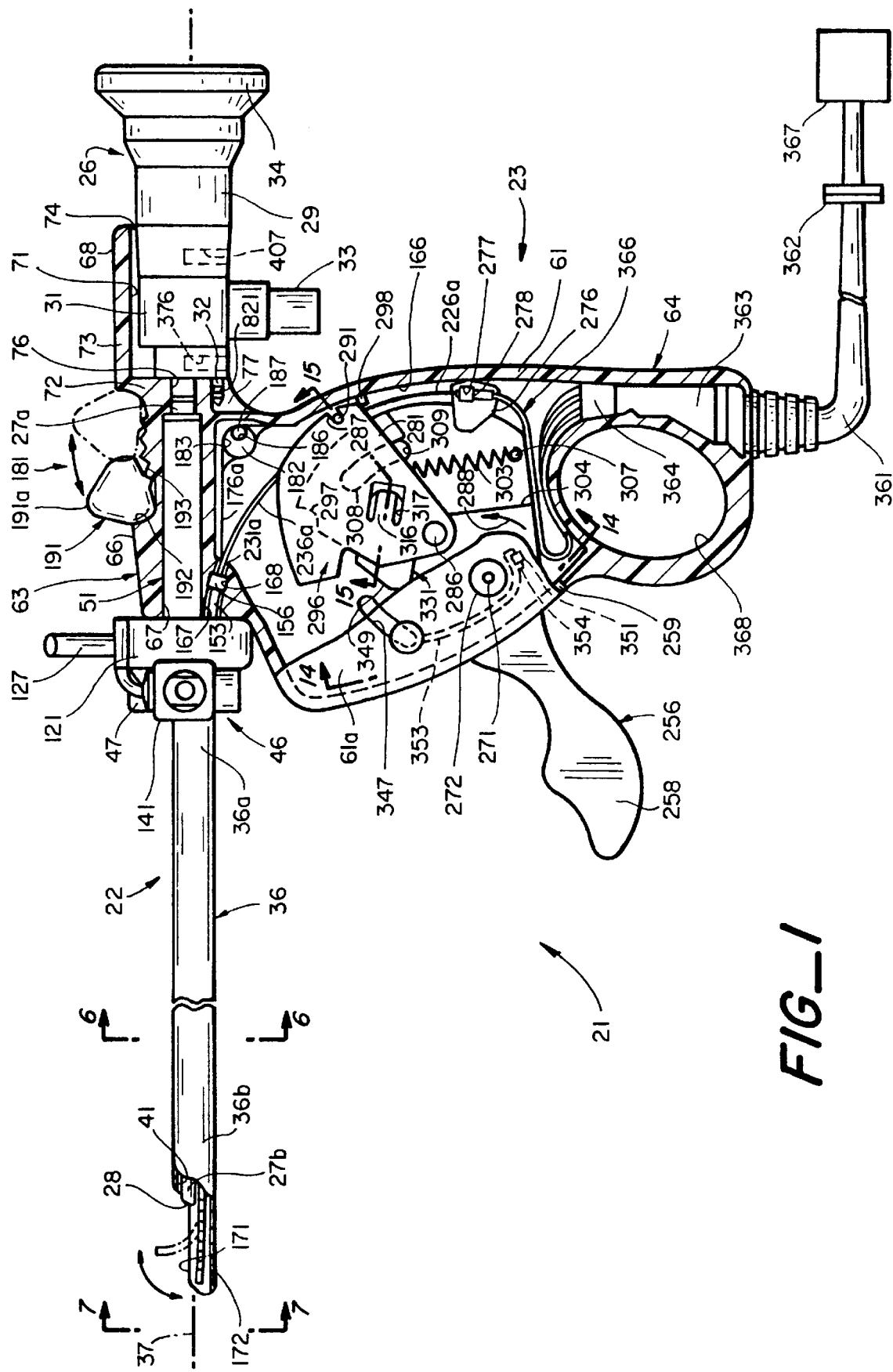

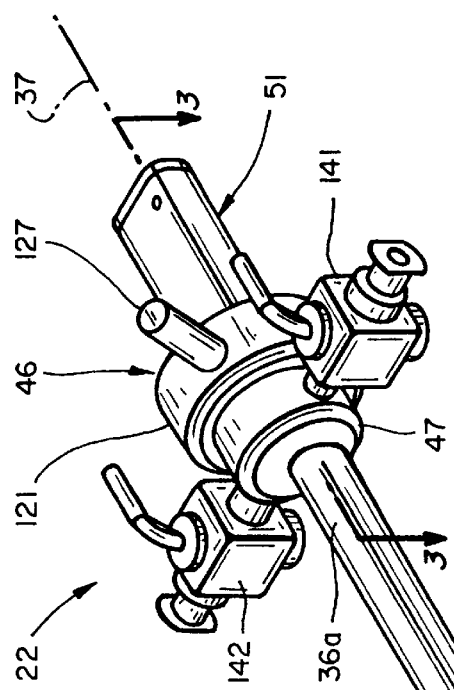
FIG_2
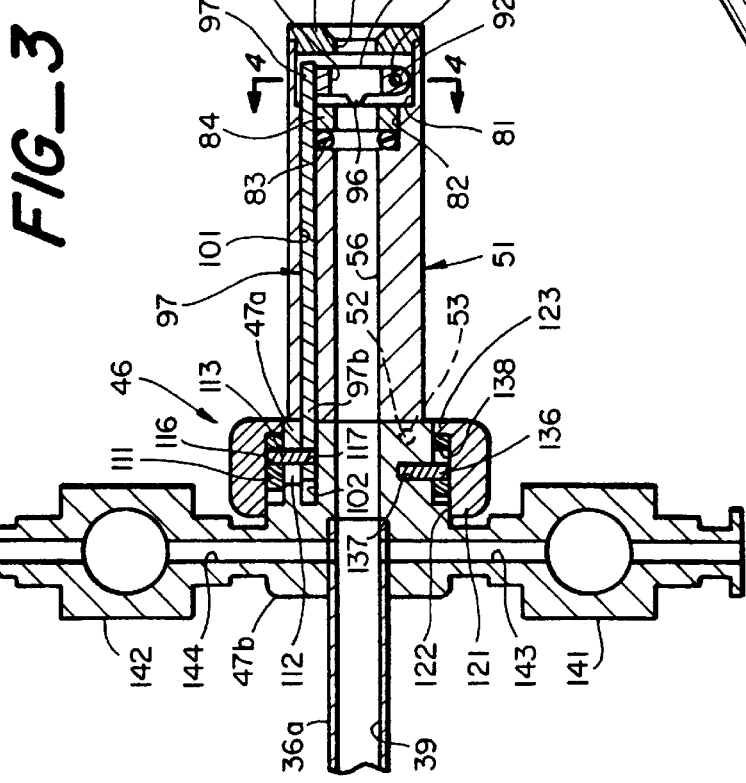
FIG_3
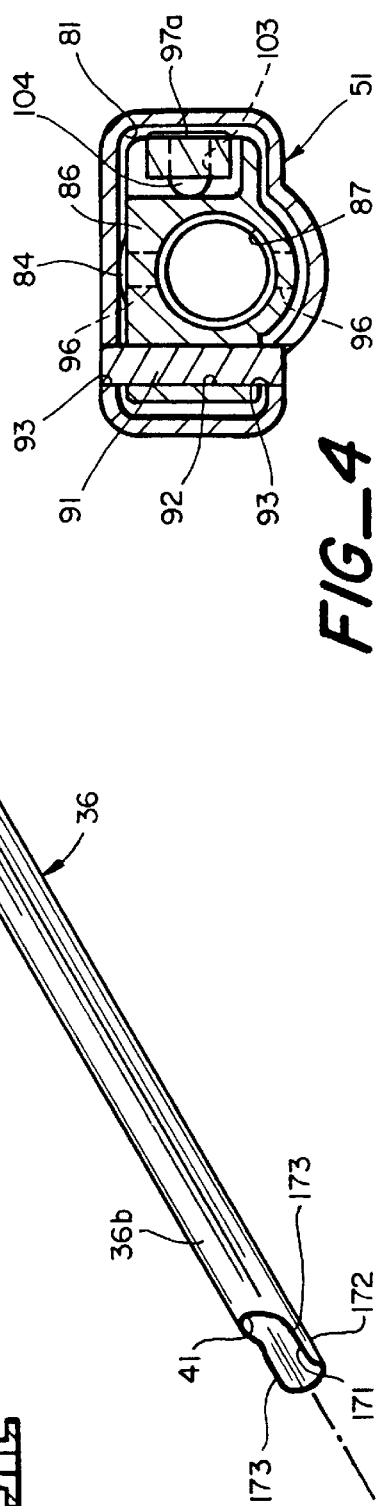
FIG_4

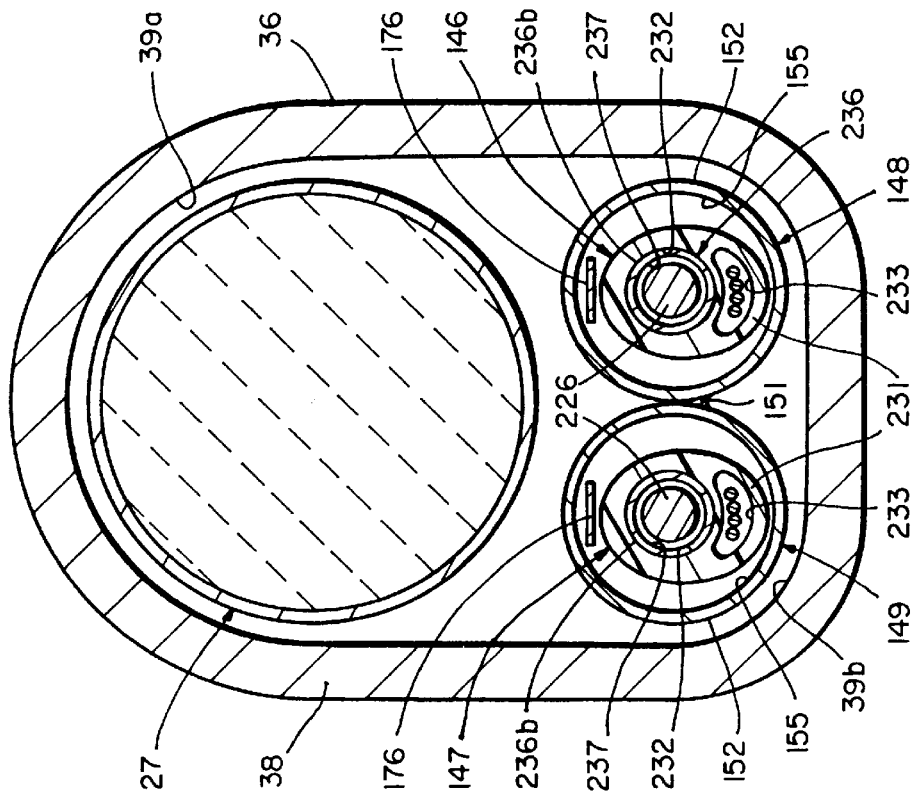
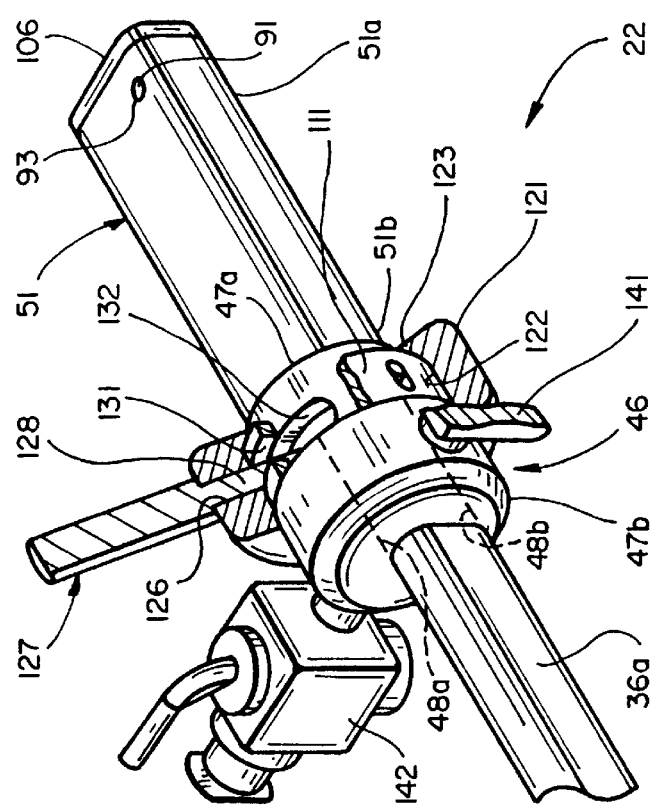

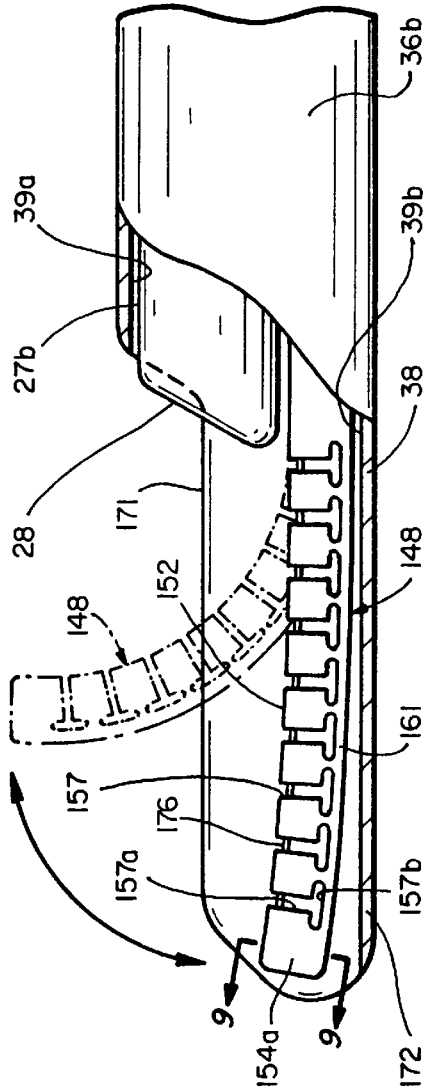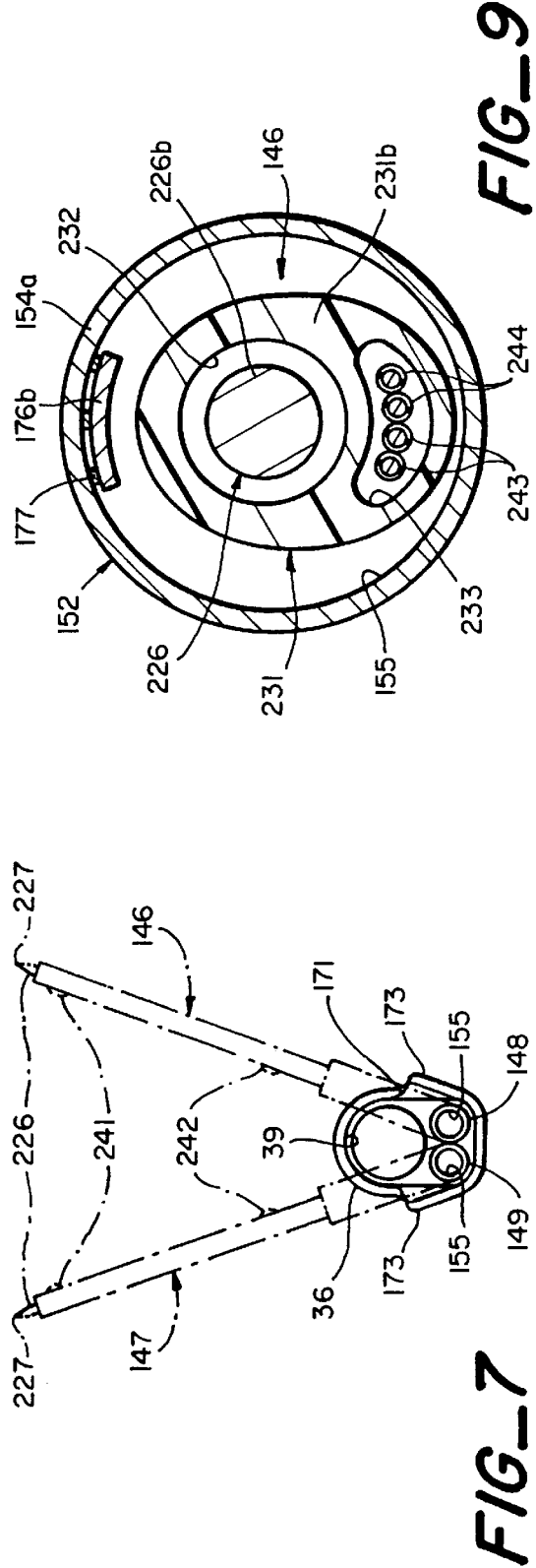

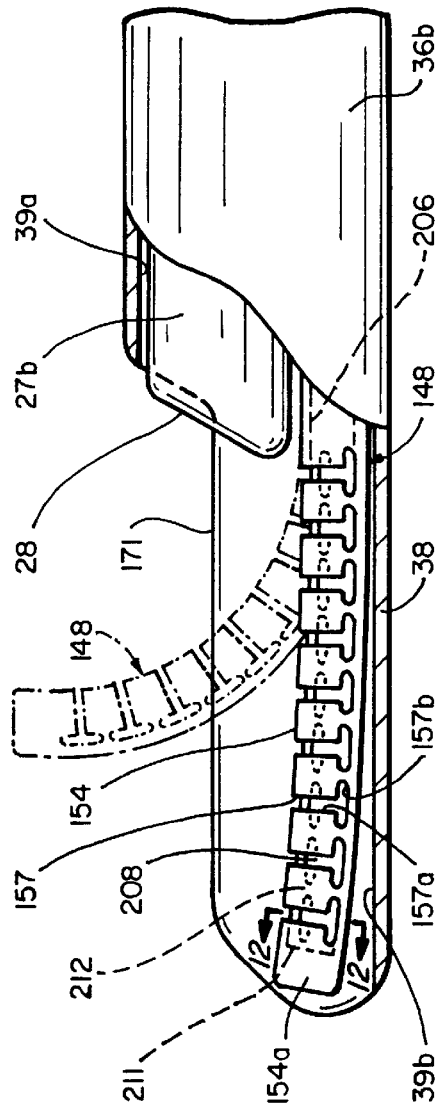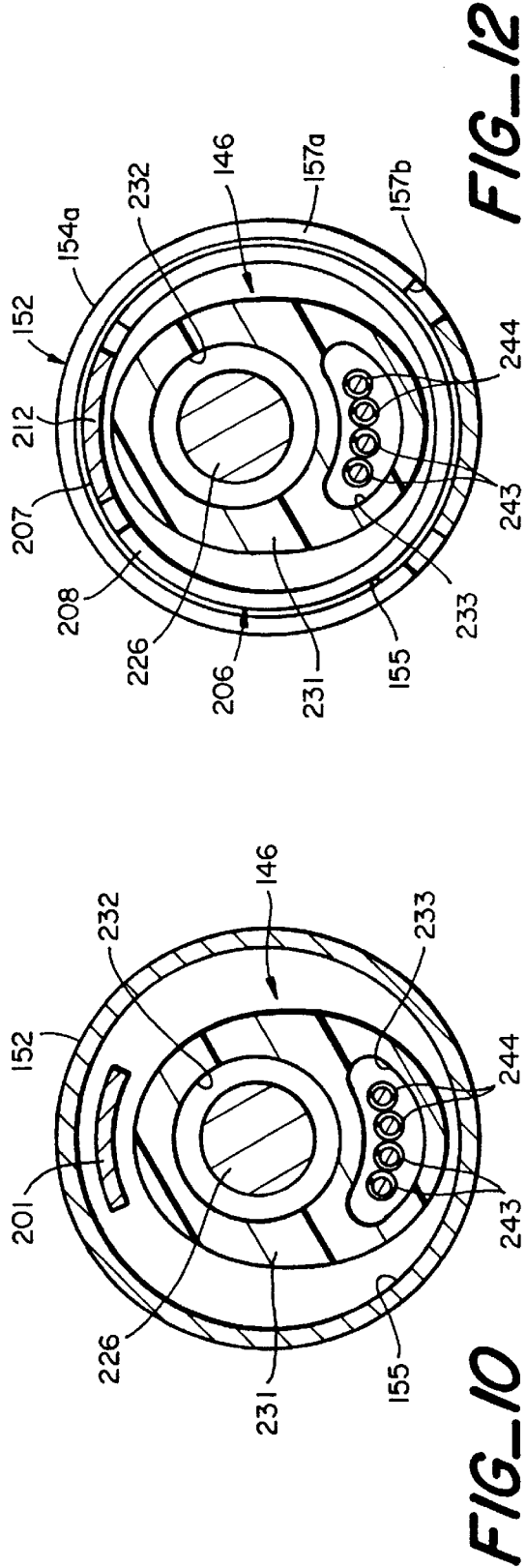

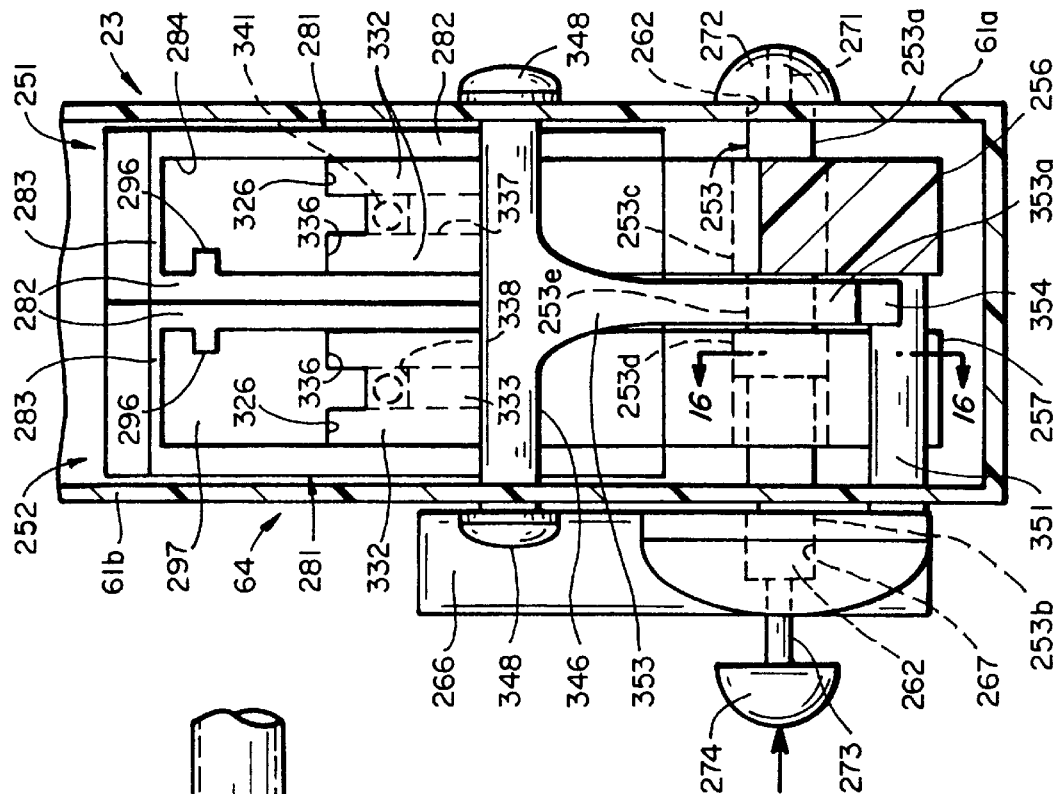
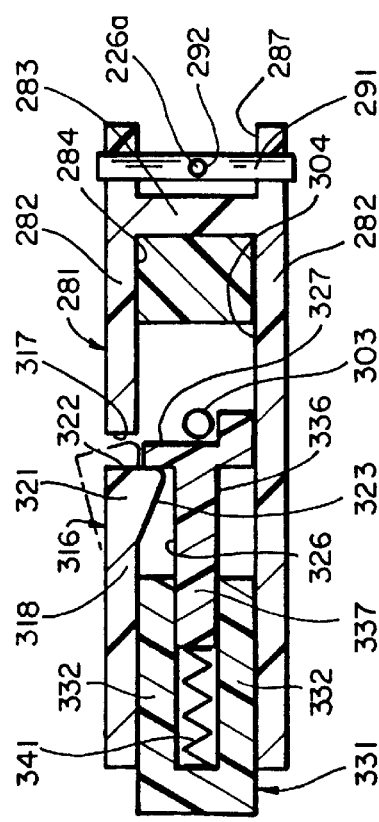

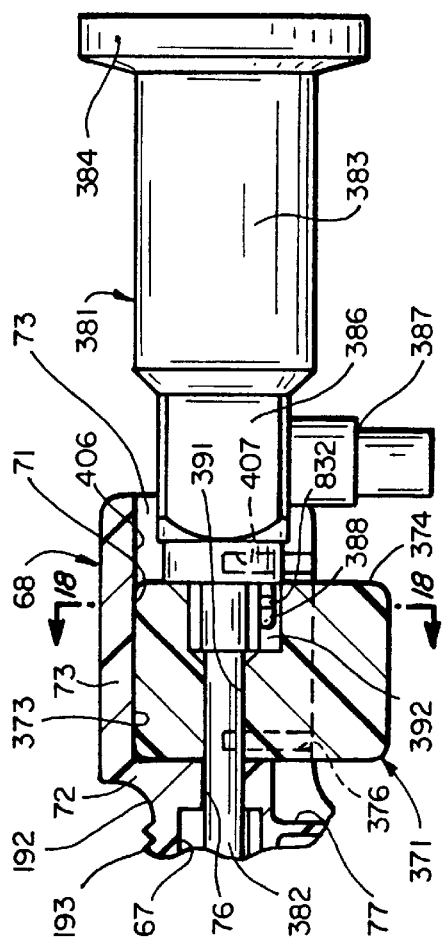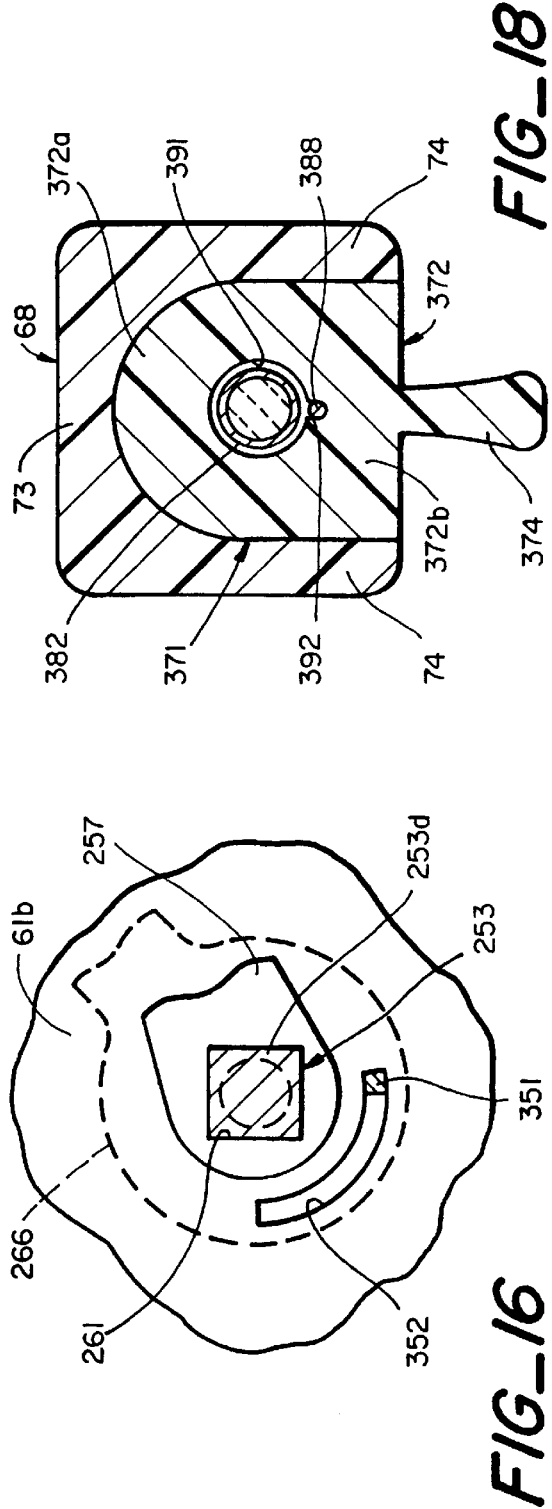

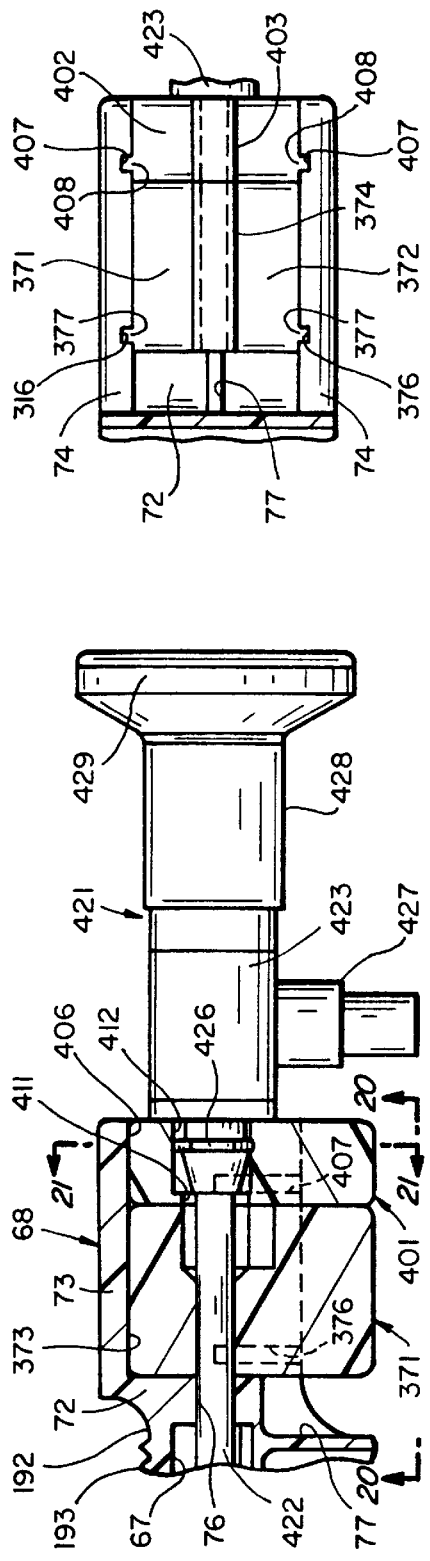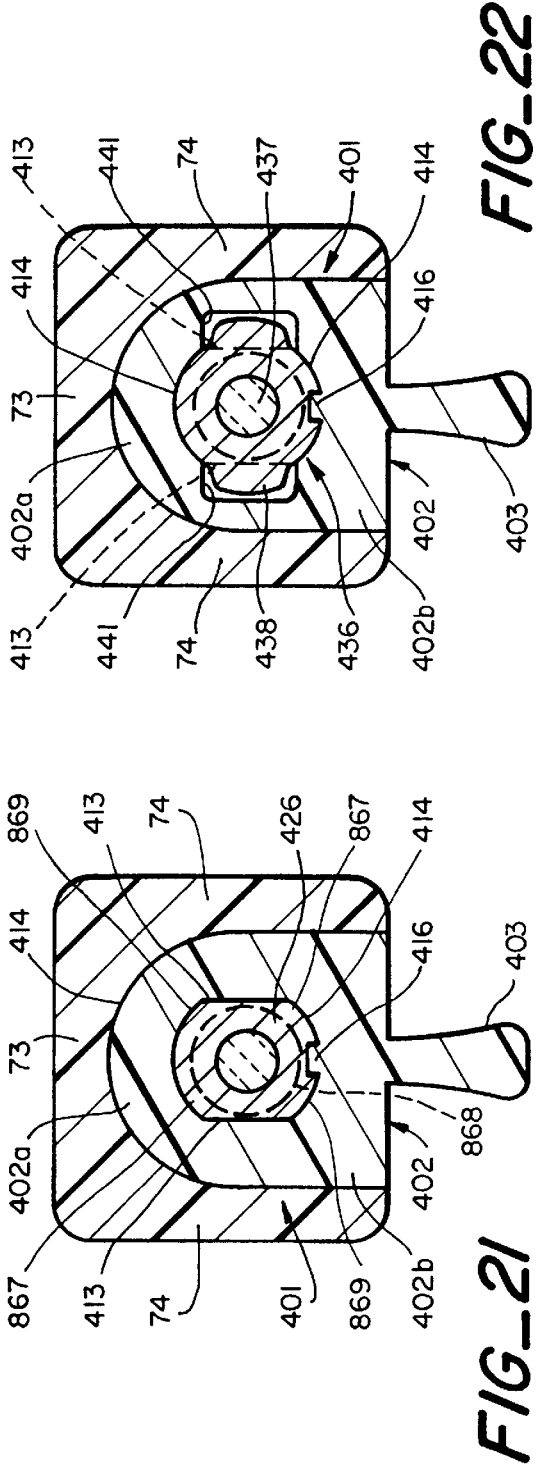

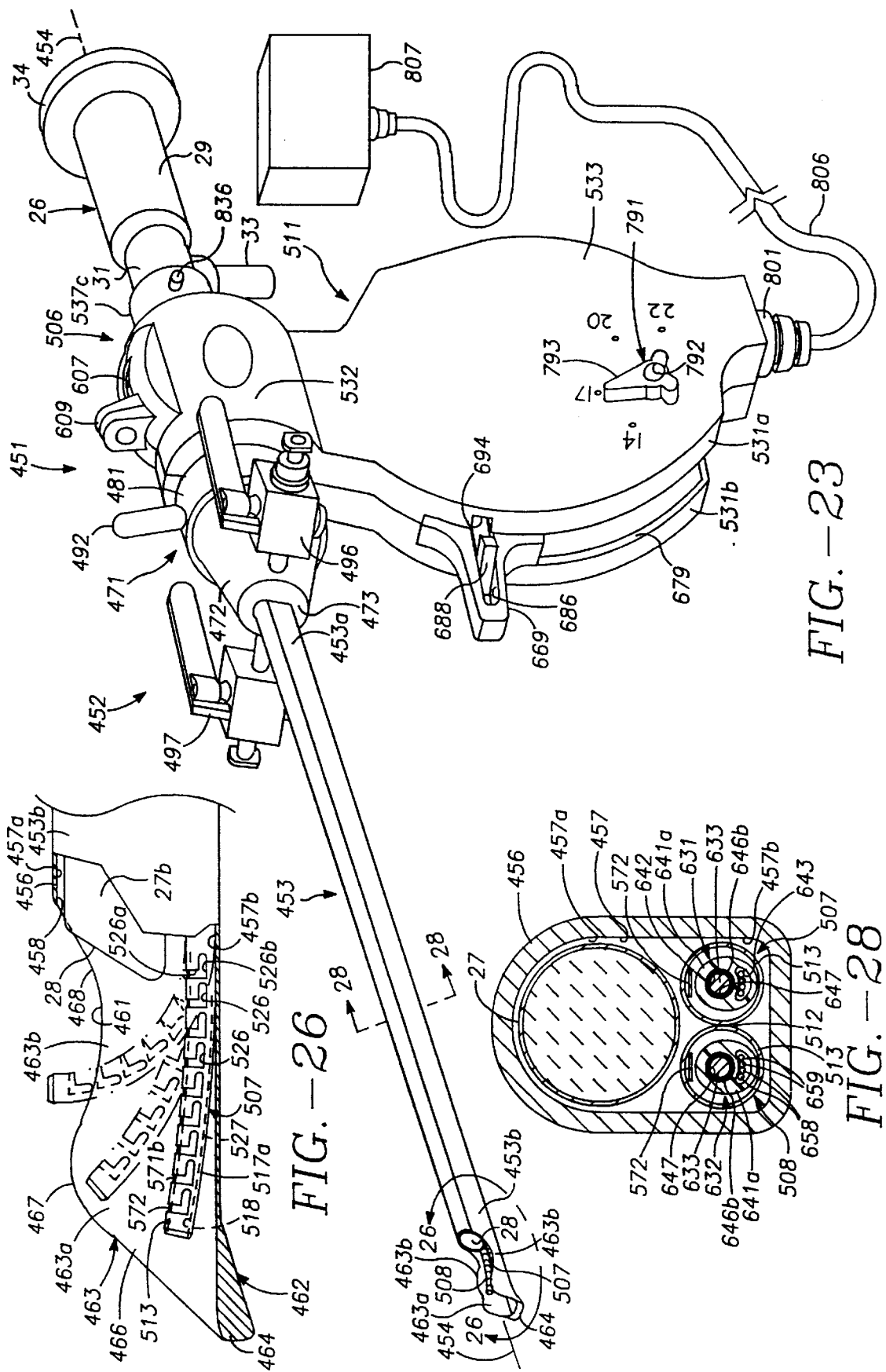

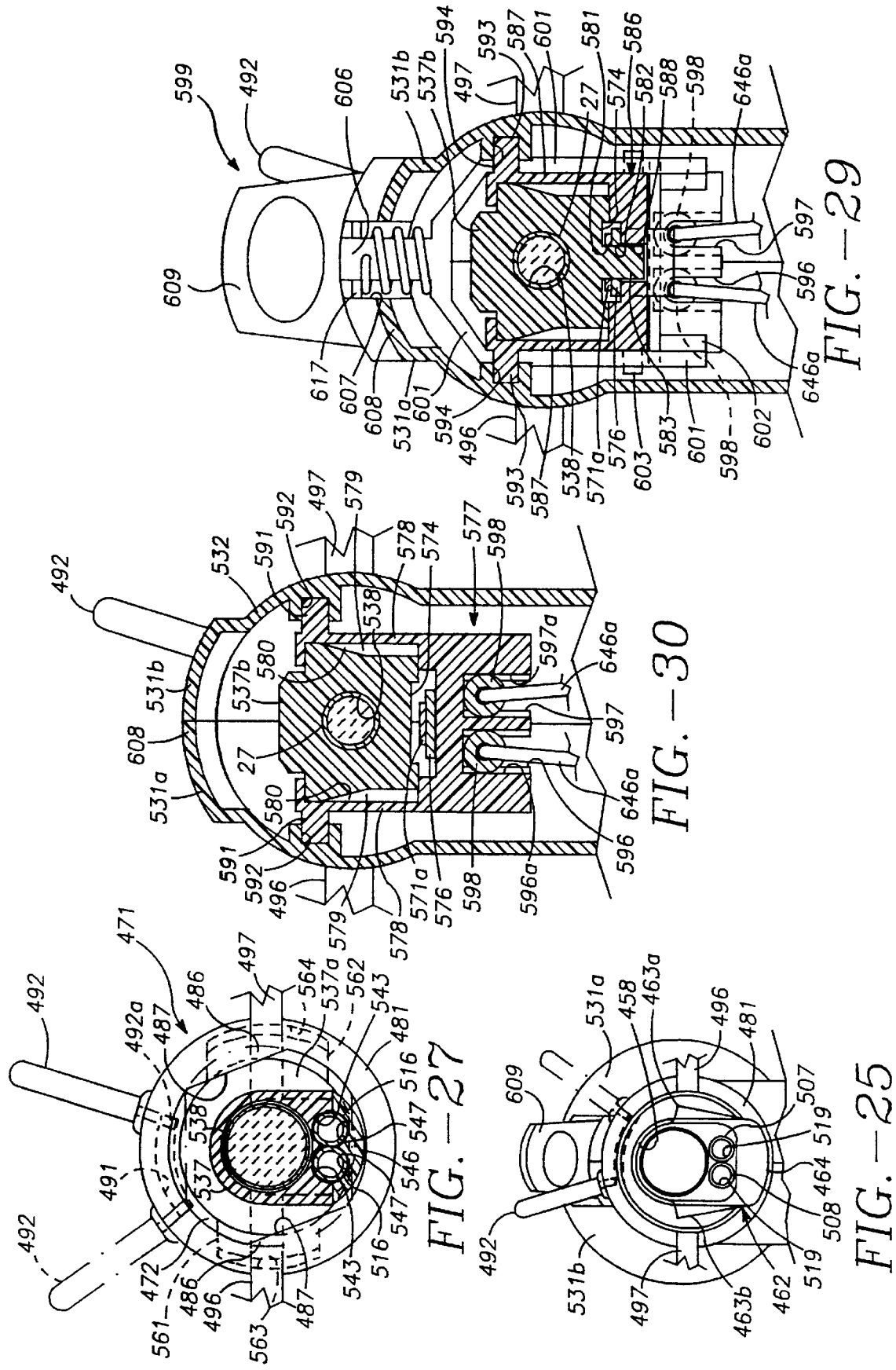

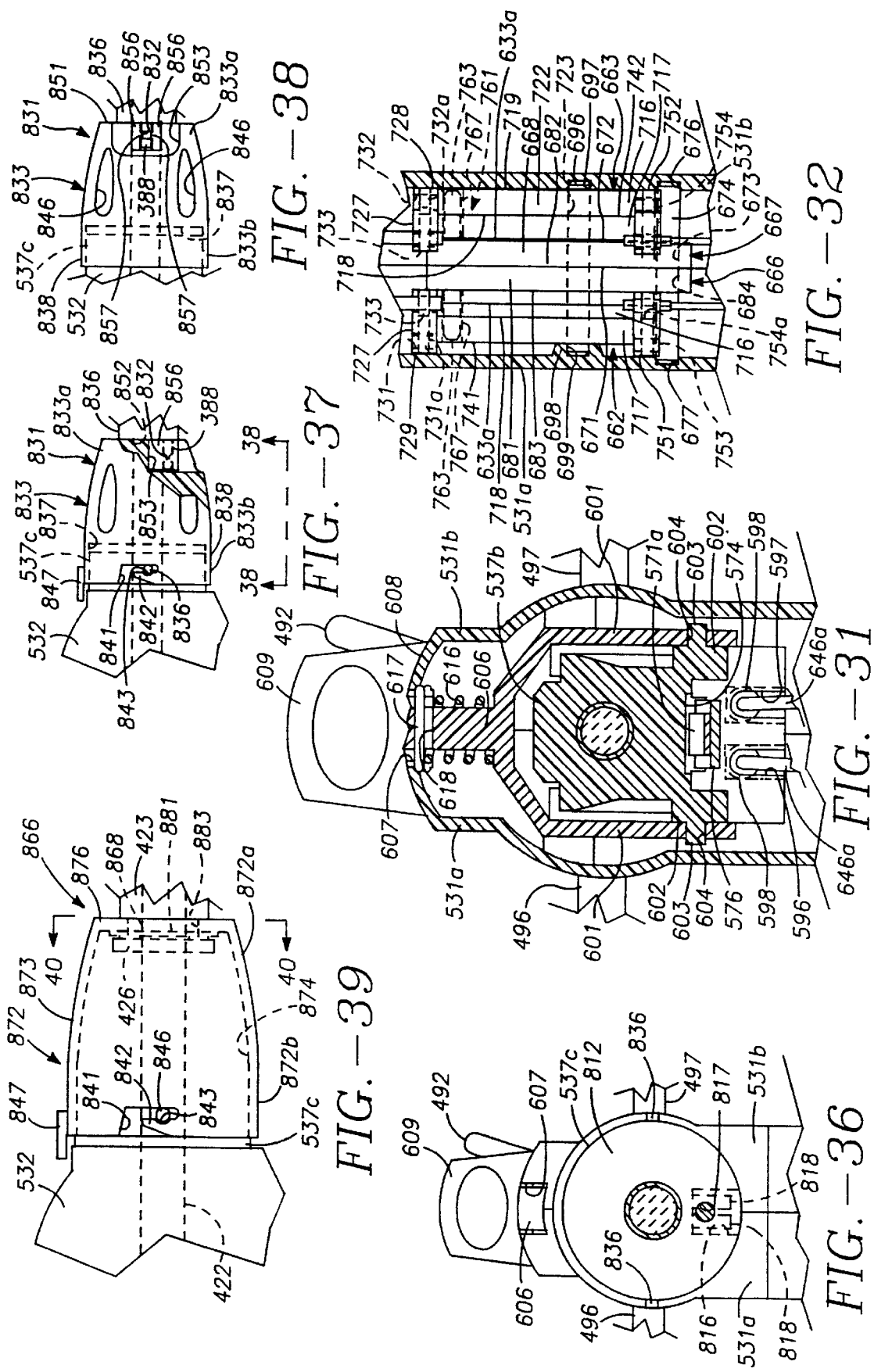

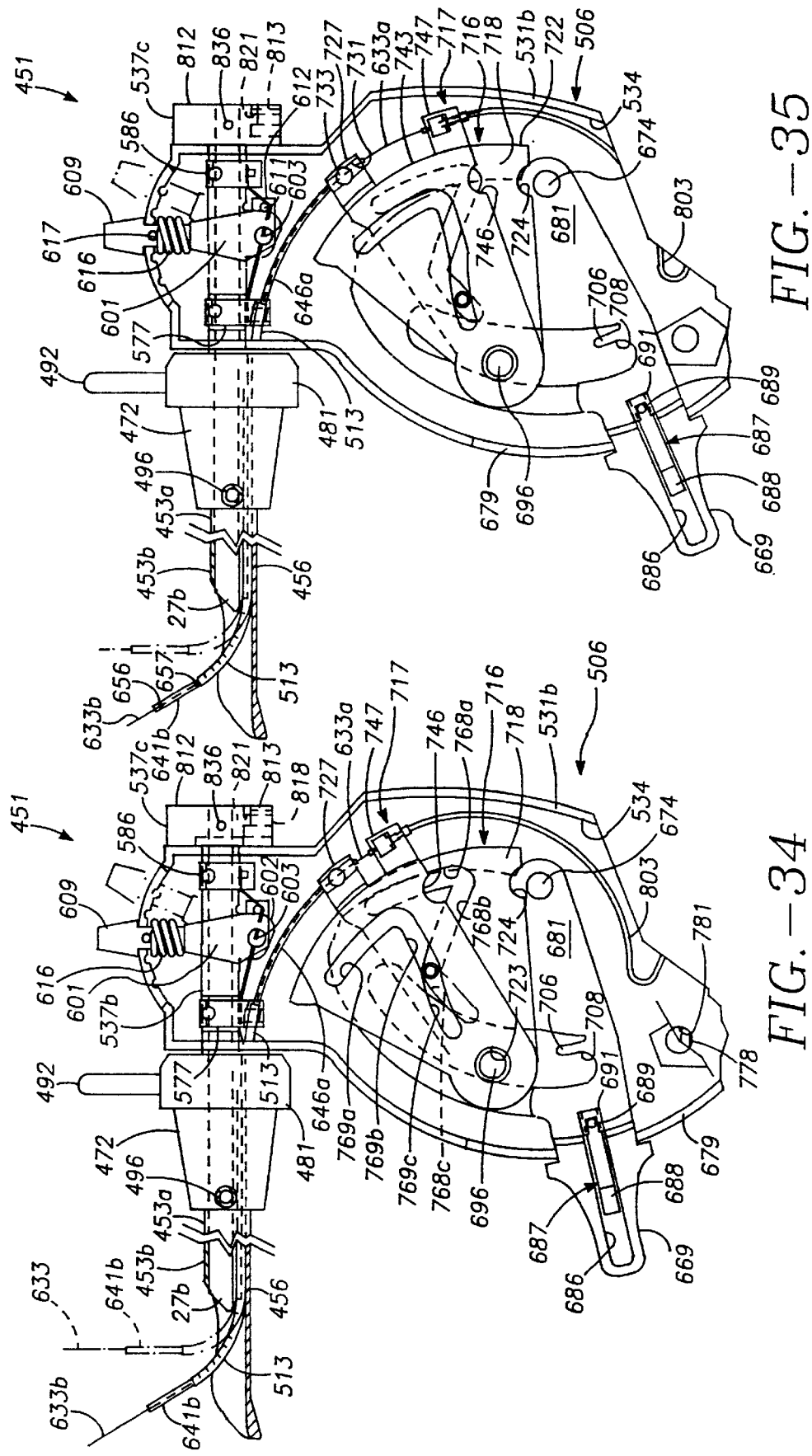

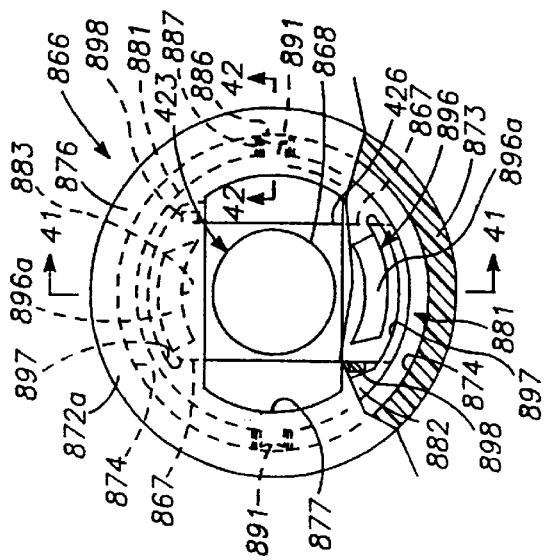
FIG.-40
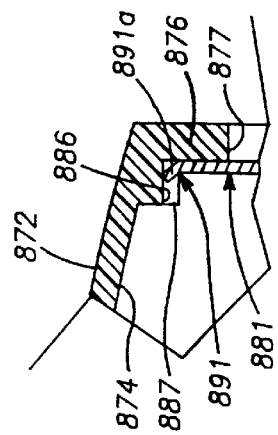
FIG.-42
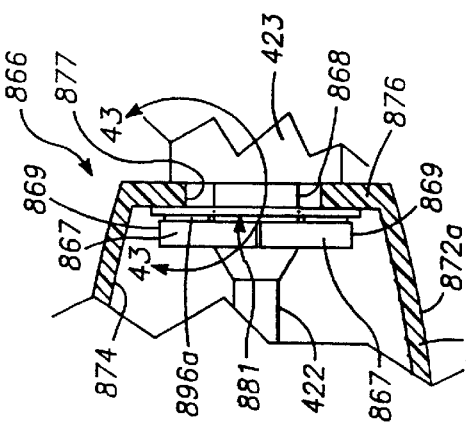
FIG.-41
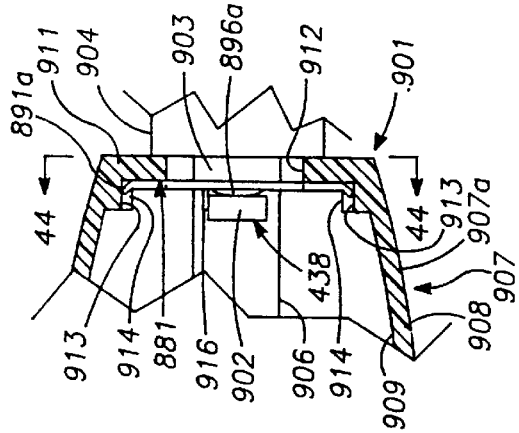
FIG.-43
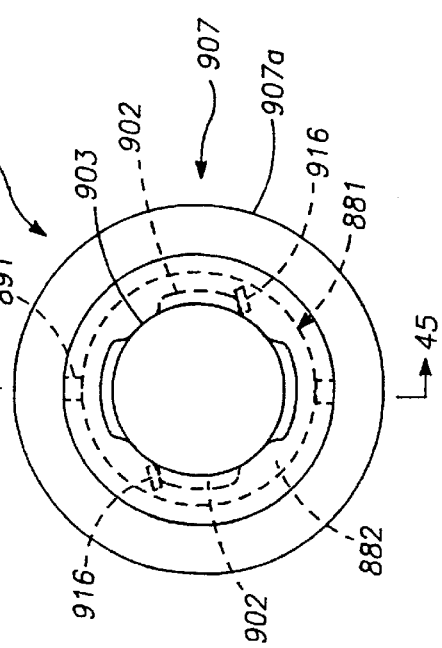
FIG.-45
FIG.-44

MEDICAL DEVICE WITH TRIGGER ACTUATION ASSEMBLY

This application is a continuation-in-part of U.S. patent application Ser. No. 08/492,272 filed Jun. 19, 1995.

This invention pertains generally to medical probe devices for use in body openings and, more particularly, to medical probe devices with scopes such as endoscopes for use in electrosurgical procedures.

Medical probe devices such as electrosurgical or electrocautery catheters have heretofore been provided for treating tissue within the human body. Devices have also been provided for performing needle ablation procedures in the prostate of a human male. These devices, however, suffer from a number of disadvantages. Among other things, many of these devices are limited in purpose or have multiple actuation elements. Many transurethral needle ablation devices, for example, have certain actuation elements dedicated to needle deployment and certain other actuation elements dedicated to deployment of an insulating sleeve mounted about the needle electrode. Some of these devices require movement of the actuation elements in a first direction for deployment of the needle electrodes and insulating sleeves and movement of the actuation elements in a second often opposite direction for retraction of the needle electrodes and insulating sleeves. There is therefore a need for a new and improved electrosurgical device which overcomes these disadvantages.

In general, it is an object of the present invention to provide an electrosurgical device which can be adapted for use with a plurality of conventional rod lens endoscopes.

Another object of the invention is to provide an electrosurgical device of the above character which includes a reusable sheath.

Another object of the invention is to provide an electrosurgical device of the above character which includes at least one needle electrode which can be advanced sidewise of the longitudinal axis of the device at a selected angle ranging from 0° to 90°.

Another object of the invention is to provide an electrosurgical device of the above character which includes a second needle electrode which can be selectively advanced or not advanced with the first needle electrode.

Another object of the invention is to provide an electrosurgical device of the above character which permits a generally unobstructed view of the needle electrodes advancing toward the target region in the body.

Another object of the invention is to provide an electrosurgical device of the above character which includes guide cannulas provided with T-shaped slots for providing a relatively smooth bend in the guide cannulas.

Another object of the invention is to provide an electrosurgical device of the above character in which a substantially rigid pull/push member is provided in the guide cannulas for bending and straightening of the guide cannulas.

Another object of the invention is to provide a device of the above character in which insulation means is coaxially disposed on the needle electrode.

Another object of the invention is to provide a device of the above character which includes an actuation element for extending and partially retracting the insulation means in a single stroke of the actuation element.

Another object of the invention is to provide a device with an actuation element of the above character which extends and partially retracts the needle electrode and the insulating means in a single stroke of the actuation element.

Another object of the invention is to provide a device of the above character which includes adjustable stop means for selectively stopping the actuation element at a predetermined position so as to limit any partial retraction of the needle electrode.

Another object of the invention is to provide a device of the above character which can be utilized for performing a transurethral needle ablation procedure.

Another object of the invention is to provide a device of the above character in which a needle electrode can be advanced into the tissue of the prostate and radio frequency energy supplied thereto for creating a lesion in the prostate.

Another object of the invention is to provide a device of the above character in which the insulation means is extended into the tissue of the prostate and then partially retracted prior to the supply of radio frequency energy thereto.

Another object of the invention is to provide a device of the above character in which the needle electrode is extended into the tissue of the prostate and then partially retracted prior to the supply of radio frequency energy to the needle electrode.

Additional objects and features of the invention will appear from the following description from which the preferred embodiments are set forth in detail in conjunction with the accompanying drawings.

FIG. 1 is a side elevational view, partially cut away, of an embodiment of the electrosurgical device of the present invention adapted for use with a first endoscope.

FIG. 2 is an isometric view of the sheath portion of the electrosurgical device of FIG. 1.

FIG. 3 is a cross-sectional view of the sheath portion of the electrosurgical device of FIG. 1 taken along the line 3—3 of FIG. 2.

FIG. 4 is a cross-sectional view of the sheath portion of the electrosurgical device of FIG. 1 taken along the line 4—4 of FIG. 3.

FIG. 5 is an enlarged view, partially cut away, of the sheath portion of the electrosurgical device of FIG. 1.

FIG. 6 is a cross-sectional view of the electrosurgical device of FIG. 1 taken along the line 6—6 of FIG. 1.

FIG. 7 is an end elevational view of the electrosurgical device of FIG. 1 taken along the line 7—7 of FIG. 1.

FIG. 8 is an enlarged side elevational view, partially cut away, of the distal extremity of the sheath portion of the electrosurgical device of FIG. 1.

FIG. 9 is a cross-sectional view of the electrosurgical device of FIG. 1 taken along the line 9—9 of FIG. 8.

FIG. 10 is a cross-sectional view, similar to FIG. 9, of another embodiment of the electrosurgical device of the present invention.

FIG. 11 is an enlarged side elevational view, similar to FIG. 8 and partially cut away, of the distal extremity of another embodiment of the electrosurgical device of the present invention.

FIG. 12 is a cross-sectional view, similar to FIG. 9, of the electrosurgical device of FIG. 11 taken along the line 12—12 of FIG. 11.

FIG. 13 is a side elevational view of a portion of another embodiment of the electrosurgical device of the present invention.

FIG. 14 is a cross-sectional view of the electrosurgical device of FIG. 1 taken along the line 14—14 of FIG. 1.

FIG. 15 is a cross-sectional view of the electrosurgical device of FIG. 1 taken along the line 15—15 of FIG. 1.

FIG. 16 is a fragmentary cross-sectional view of the electrosurgical device of FIG. 1 taken along the line 16—16 of FIG. 14.

FIG. 17 is a fragmentary cross-sectional view of the proximal portion of the electrosurgical device of FIG. 1 adapted for use with a second cystoscope.

FIG. 18 is a cross-sectional view of the electrosurgical device of FIG. 17 taken along the line 18—18 of FIG. 17.

FIG. 19 is a fragmentary cross-sectional view of the proximal portion of the electrosurgical device of FIG. 1 adapted for use with a third cystoscope.

FIG. 20 is a bottom plan view of the electrosurgical device of FIG. 19 taken along the line 20-20 of FIG. 19.

FIG. 21 is a cross-sectional view of the electrosurgical device of FIG. 19 taken along the line 21—21 of FIG. 19.

FIG. 22 is a cross-sectional view, similar to FIG. 21, of the proximal portion of the electrosurgical device of FIG. 1 adapted for use with a fourth cystoscope.

FIG. 23 is an isometric view of another embodiment of the electrosurgical assembly or transurethral needle ablation assembly of the present invention.

FIG. 25 is an end elevational view of the electrosurgical assembly of FIG. 23 taken along the line 25—25 of FIG. 24.

FIG. 26 is an enlarged side elevational view, partially cut away, of the electrosurgical assembly of FIG. 23 taken along the line 26—26 of FIG. 23.

FIG. 27 is a cross-sectional view of the electrosurgical assembly of FIG. 23 taken along the line 27—27 of FIG. 24.

FIG. 28 is a cross-sectional view of the electrosurgical assembly of FIG. 23 taken along the line 28—28 of FIG. 23.

FIG. 29 is a cross-sectional view of the electrosurgical assembly of FIG. 23 taken along the line 29—29 of FIG. 24.

FIG. 30 is a cross-sectional view of the electrosurgical assembly of FIG. 23 taken along the line 30—30 of FIG. 33.

FIG. 31 is a cross-sectional view of the electrosurgical assembly of FIG. 23 taken along the line 31—31 of FIG. 33.

FIG. 32 is a cross-sectional view of the electrosurgical assembly of FIG. 23 taken along the line 32—32 of FIG. 24.

FIG. 34 is a segmented side elevational view, similar to FIG. 33, of the electrosurgical assembly of FIG. 23 in yet another position.

FIG. 35 is a segmented side elevational view, similar to FIG. 33, of the electrosurgical assembly of FIG. 23 in a further position.

FIG. 36 is a cross-sectional view of the electrosurgical assembly of FIG. 23 taken along the line 36—36 of FIG. 24.

FIG. 37 is a side elevational view, partially cut away, of a portion of another embodiment of the electrosurgical assembly of the present invention.

FIG. 38 is a bottom plan view of the electrosurgical assembly of FIG. 37 taken along the line 38—38 of FIG. 37.

FIG. 39 is a side elevational view of a portion of another embodiment of the electrosurgical assembly of the present invention.

FIG. 40 is a cross-sectional view, partially cut away, of the electrosurgical assembly of FIG. 39 taken along the line 40—40 of FIG. 39.

FIG. 41 is a cross-sectional view of the electrosurgical assembly of FIG. 39 taken along the line 41—41 of FIG. 40.

FIG. 42 is a cross-sectional view of the electrosurgical assembly of FIG. 39 taken along the line 42—42 of FIG. 40.

FIG. 43 is an enlarged view, partially cross-sectioned, of the electrosurgical assembly of FIG. 39 taken along the line 43—43 of FIG. 41.

FIG. 44 is a cross-sectional view, similar to FIG. 40, of a portion of another embodiment of the electrosurgical assembly of the present invention.

FIG. 45 is a cross-sectional view of the electrosurgical assembly of FIG. 44 taken along the line 45—45 of FIG. 44.

Figure 24:
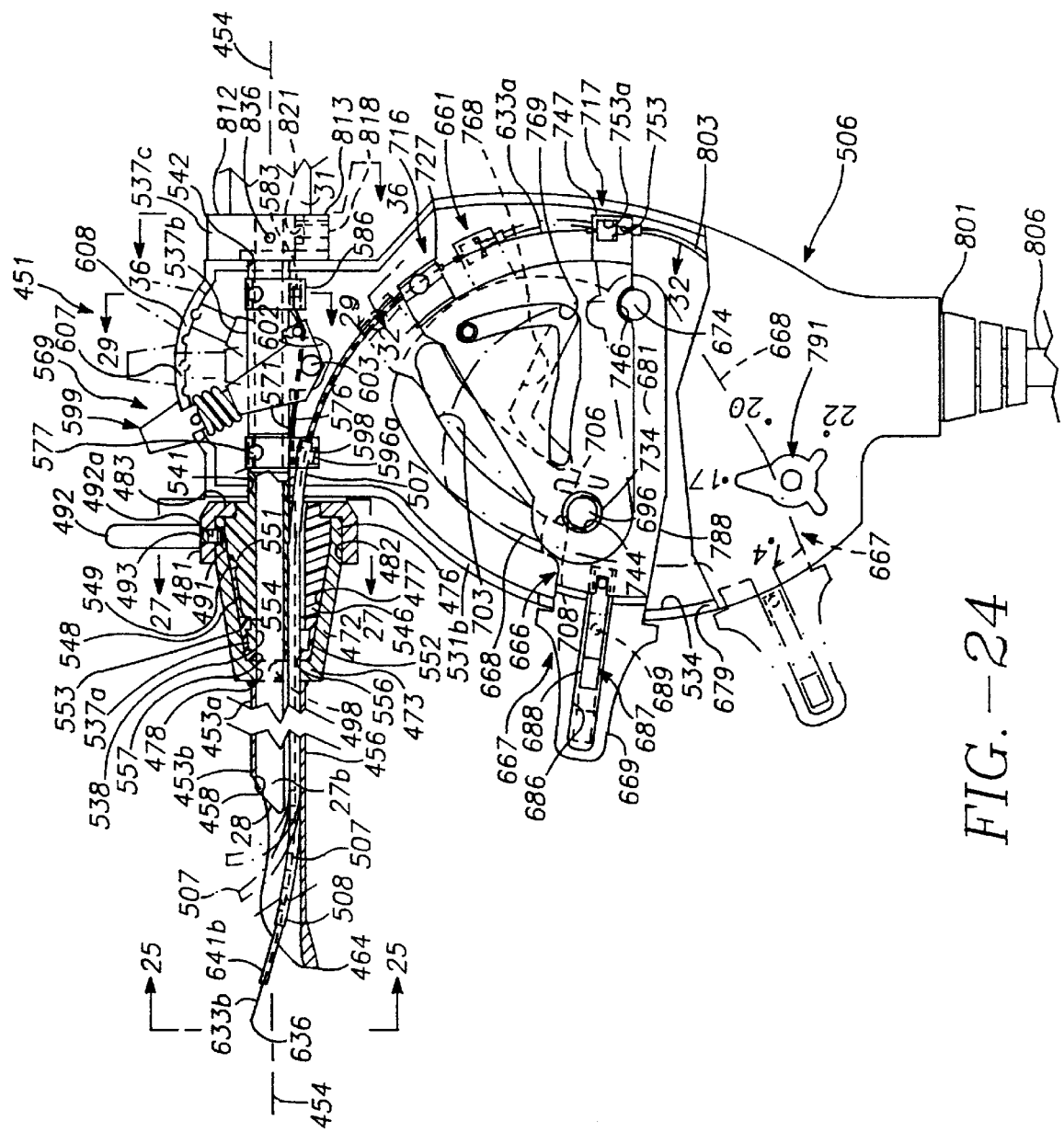
FIG. 24 is a segmented side elevational view, partially cross-sectioned, of the electrosurgical assembly of FIG. 23.

In general, an electrosurgical device for medical treatment of tissue at a treatment site through a body opening is provided. The device includes a sheath having proximal and distal extremities and having a passageway extending from the proximal extremity to the distal extremity. A guide tube is slidably mounted in the passageway of the sheath and has proximal and distal extremities and a lumen extending from the proximal extremity to the distal extremity. A needle electrode is slidably mounted in the lumen of the guide tube and has proximal and distal extremities. Insulation means is coaxially disposed on the needle electrode. A handle adapted to be gripped by the human hand and means for mounting the proximal extremity of the guide tube on the handle are provided. Means is carried by the handle for causing bending of the distal extremity of the guide tube at an angle with respect to the longitudinal axis whereby the lumen in the guide tube can be directed so that it faces the tissue to be treated. Means is connected to the needle electrode adapted to be coupled to an energy source for supplying energy to the needle electrode. Means is carried by the handle and coupled to the needle electrode and the insulation means for advancing and retracting the needle electrode and the insulation means with respect to the guide tube and includes a single actuation element movable in a single stroke from a first position in which the needle electrode and the insulation means are disposed within the guide tube and a second position in which the needle electrode and the insulation means are disposed in the tissue at the treatment site. A method for using the device is provided.

More in particular, electrosurgical device or catheter 21 of the present invention includes sheath means in the form of sheath portion or sheath 22 and handle means in the form of handle portion or handle 23 (see FIG. 1). Electrocautery or electrosurgical catheter 21 is adapted for use with a plurality of different endoscopes such as conventional endoscope 26 made by Olympus Corporation for cystoscopy. Endoscope 26, in general, includes an elongate optical element 27 having proximal and distal extremities 27a and 27b. Optical element 27 has a distal viewing face 28 inclined at an oblique angle of approximately 30° relative to the longitudinal axis of the optical element. Optical element 27 is provided with an axially-extending central rod lens concentrically surrounded by a plurality or bundle of light fibers shown generally and collectively in FIG. 6 and enclosed by a protective rigid tubular sheath made from any suitable material such as stainless steel. Endoscope 26 has a proximal portion which includes lens housing 29 interconnected to proximal extremity 27a of optical element 27 by fitting 31. The fitting 31 is formed with a distally projecting coupling extension 32 and is further provided with a light post 33 for permitting a suitable light source to be connected to the bundle of optical light fibers carried within optical element 27. Lens housing 29 is further provided with an eyepiece 34.

Sheath 22, as illustrated separately in FIG. 2, includes an elongate tubular member or tube 36 having proximal and distal extremities 36a and 36b. Substantially rigid tube 36 can be of any suitable type and size, as for example, a 23 French catheter-like guide housing having a length of approximately nine inches and can be formed of a suitable material such as stainless steel. Tube 36 extends along a central longitudinal axis 37 and has an external or outer cylindrical wall 38 for forming an internal lumen or passageway 39 which extends from proximal extremity 36a to an opening 41 at distal extremity 36b. Passageway 39 is generally oblong in cross-section, as illustrated in FIG. 6, and includes an upper portion 39a and a lower portion 39b.

A locking assembly 46 is mounted to proximal extremity 36a of a tube 36 (see FIGS. 3–5). Locking assembly 46 includes a distal member in the form of a cylindrical member or hub 47 made from any suitable material such as brass and provided with a bore 48 which extends longitudinally therethrough. Bore 48 is generally oblong in cross-section and has an upper portion 48a and a lower portion 48b. The bore 48 has an enlarged distal portion for receiving proximal extremity 36a. The tube 36 is joined to hub 47 by brazing or any other suitable means. Hub 47 has a length of approximately 0.7 inch and is formed with a proximal portion 47a and a distal portion 47b which are each circular in cross-section. Distal portion 47b has an outer diameter of approximately 0.70 inch and proximal portion 47a is of reduced diameter relative to the distal portion 47b with an outer diameter of approximately 0.56.

Locking assembly 46 further includes a proximal member in the form of an optic lock block 51 made from brass or any other suitable material and having proximal and distal end portions 51a and 51b. Block 51 has a length of approximately 1.5 inch. Spaced-apart first and second dowels 52 extend longitudinally from the distal end portion 51b of block 51 and are cooperatively received within similarly spaced-apart first and second longitudinally-extending bores 53 extending into hub proximal portion 47a for assisting in the mounting of block 51 to hub 47. Block 51 extends proximally from hub 47 along longitudinal axis 37 and is joined to the hub by any suitable means such as brazing. The block 51 is provided with a central bore 56 extending between proximal and distal end portions 51a and 51b which communicates with bore upper portion 48a of the hub 47. Stopcock hub 47 and optic lock block 51 are nickel plated to seal the brass material of these elements and to give locking assembly 46 a uniform cosmetic as well as functional outer coating.

Handle 23 is adapted to secure endoscope 26 to sheath 22. The handle 23 has an outer shell 61 made from a suitable material such as polycarbonate and formed from a first or left side portion 61a and a second or right side portion 61b as illustrated in FIGS. 1 and 14. Handle 23 includes coupling means in the form of coupling portion 63 for interconnecting handle 23 to sheath 22 and a depending portion 64 for grasping by a human hand. Coupling portion 63 mounts to the proximal portion of sheath 22 and extends along longitudinal axis 37. Depending portion 63 extends at a right angle to axis 37 when the handle 23 is mounted to sheath 22. Coupling portion 63 has a distal section 66 formed with a longitudinally-extending internal socket 67 which is sized and shaped to cooperatively receive optical lock block 51 with a slip fit. Coupling portion 63 further includes an inverted U-shaped proximal section 68 provided with an internal recess 71 formed by a transversely-extending internal wall 72, a top wall 73 extending proximally from internal wall 72 and spaced-apart first and second side walls 74 extending proximally from the internal wall 72 and depending from the top wall 73. A longitudinally-extending bore 76 extends through internal wall 72 from internal recess 71 into socket 67 and is aligned so as to communicate with central bore 56 of the optic lock block 51.

Internal recess 71 is sized and shaped to cooperatively receive fitting 31 and at least a portion of lens housing 29 of endoscope 26 (see FIG. 1). Fitting 31 abuts internal wall 72 and optical element 27 extends through bore 76 into bore 53 of the optic lock block 51, upper portion 48a of hub bore 48 and upper portion 39a of tube passageway 39.

Internal wall 72 is included within the first adapter means of coupling portion 63 for engaging first coupling extension or coupling extension 32 of endoscope 26. Wall 72 and sheath 22 are longitudinally sized so that distal extremity 27b of the endoscope 26 extends within upper portion 39a of passageway 39 to a point adjacent and generally aligned with tube opening 41. Internal wall 72 is also included within the first cooperative means of coupling portion 63 for mating with coupling extension 32 to restrict rotation of endoscope 26 about longitudinal axis 37. As illustrated in FIGS. 1 and 19, the internal wall 72 is formed with a locking recess 77 which receives endoscope coupling extension 32 and thereby limits rotational movement of the endoscope within coupling portion 63 and sheath 22. First locking recess 77 is angularly aligned about the longitudinal access 37 so that when coupling extension 32 is disposed therein, oblique viewing face 28 is inclined upwardly away from lower portion 39b of passageway 39.

Locking assembly 46 is included within means carried by proximal extremity 36a of tube 36 for gripping optical element 27 to secure endoscope 26 within sheath 22 and thus secure handle 23 to the sheath and endoscope. As illustrated in FIG. 3, proximal end portion 51a of block 51 is provided with an enlarged recess 81 and an annular groove 82 where central bore 56 opens into recess 81. An annular flexible element made from an elastomeric material in the form of optic-lock O-ring 83 is pressed into annular groove 82 and backed by an annular washer-like element in the form of an optic lock washer 84 made from any suitable material such as stainless steel and also disposed within annular groove 82.

Means is included within locking assembly for compressing O-ring 83 so to cause the O-ring to expand against optical element 27. The enlarged recess 81 is sufficiently sized for transversely receiving a clamping member in the form of optic lock yoke 86 made from any suitable material such as stainless steel and provided with a centrally disposed bore 87 extending longitudinally therethrough for receiving endoscope optical element 27 (see FIGS. 3 and 4). Yoke 86 is pivotly retained within recess 81 by a cylindrical pin 91 disposed in a second bore 92 extending through a first end of optic lock yoke 86 in a direction perpendicular to central bore 87. Pin 91 is press fit or otherwise suitably secured at each end within a bore 93 extending through proximal end portion 51a of block 51 and recess 81 provided therein. Yoke 86 is provided with first and second protuberances 96 which are diametrically disposed about a central bore 87 in the yoke. Protuberances 96 extend forwardly from the distal surface of yoke 86 and engage the top and bottom of lock washer 84.

Means is included for pivoting optic lock yoke 86 about the axis of pin 91 and includes an elongate member or drawbar 97, illustrated in FIGS. 3 and 4, made from stainless steel or any other suitable material and having proximal and distal end portions 97a and 97b. Drawbar 97 is disposed in a cooperatively sized second elongate bore 101 extending through optic lock block 51 in parallel disposition to central bore 56 and protrudes into a second similarly aligned and sized bore 102 extending into proximal portion 47a of hub 47 in parallel disposition to bore 48 of the hub. Drawbar proximal end portion 97a is hammerhead in conformation so as to have a narrowed portion 103 for disposition within a cutout 104 formed by spaced-apart first and second extensions on the opposite end of yoke 86 from second bore 92 (see FIG. 4). Proximal end portion 97a of the drawbar 97 rides against the inner wall forming enlarged recess 81 which serves to retain narrowed portion 103 within cutout 104 during axial movement of the drawbar within block 51 and hub 47. An end cap 106 made from nickel plated brass or any other suitable material extends over the opening of enlarged recess 81 and is secured to proximal end portion 51a of block 51 by brazing or any other suitable means. A bore 107 for receiving optical element 27 extends through end cap 106 and is axially aligned with the central bore 56 of block 51.

Means for causing drawbar 97 to slide proximally and distally within optic lock block 51 so as to pivot optic lock yoke 86 includes a first and inner annular member or ring 111 made from stainless steel or any other suitable material. Linear slip ring 111 is diametrically sized so as to slidably extend around hub proximal portion 47a generally flush with hub distal portion 47b (see FIG. 3). Hub proximal portion 47a is provided with an elongate slot 112 which extends alongside the hub into second bore 102. A first radially extending pin 113 extends through the elongate slot 112 and is press fit or otherwise suitably secured at its outer end within a radially extending bore 116 in ring 111 and press fit or otherwise suitably secured at its opposite inner end within a bore 117 extending through distal end portion 97b of the drawbar 97.

Locking assembly 46 includes a second annular member or ring in the form of optic lock collar 121 made from a suitable material such as stainless steel and provided with a central opening 122 extending therethrough. Collar 121 has an internal diameter slightly larger than the external diameters of hub distal portion 47b and slip ring 111 so as to permit the collar to rotatably extend around slip ring 111 and over a portion of hub distal portion 47b. Collar 121 is formed with a proximal flange 123 which extends inwardly into opening 122 and is internally sized for rotatable disposition about hub proximal portion 47a. A radial bore 126 is provided in collar 121 and a radially-extending lever or radius bar 127 is threaded or otherwise suitably secured within bore 126. Radius bar 127 includes a radial extension 128 which extends inwardly into central opening 122 through a helically-extending slot 131 provided in linear slip ring 111 and into a circumferentially-extending slot 132 provided in hub proximal portion 47a. The disposition of radial extension 128 in slot 132 of hub proximal portion 47a longitudinally fixes optic lock collar 121 relative to hub 47.

As can be appreciated by those skilled in the art, rotation of collar 121 relative to hub 47, by means of radius bar 127 or otherwise, causes bar extension 128 to move through helical slot 131 to thus cause linear slip ring 111 trapped between collar 121 and hub proximal portion 47a to move longitudinally relative to the collar 121 and hub 47. Slip ring 111 is longitudinally sized smaller than hub proximal portion 47a to permit travel of the slip ring over the proximal portion 47a. By so causing slip ring 111 to move toward hub distal portion 47b, yoke protuberances 96 are pressed against washer 84 under the force of drawbar 97 so as to compress O-ring 83 and cause it to expand radially inwardly and circumferentially grip optical element 27 of endoscope 26. A second radially extending pin 136 press fit or otherwise suitably secured within a radially provided bore 137 in hub proximal portion 47a and projecting outwardly into a longitudinally-extending slot 138 formed in linear slip ring 111 further assists in restricting rotation of slip ring 111 relative to hub 47.

First and second stopcocks 141 and 142 are provided on sheath 22 for permitting any suitable liquid such as a flushing fluid to be introduced into and withdrawn from sheath passageway 39. The stopcocks 141 and 142 can be of any conventional type such as those made by Popper and Sons of New Hyde Park, N.Y. Distal portion 47b of hub 47 is provided with first and second radially extending bores 143 and 144 which extend into hub bore 48. The first and second stopcocks 141 and 142 are attached to hub distal portion 47b so as to communicate with respective first and second bores 143 and 144 and thus tube passageway 39. The bores 143 and 144 extend along a diameter of hub 47 and the stopcocks 141 and 142 are on opposite sides of sheath 22. Optic lock O-ring 83 additionally serves as a fluid tight seal within optic lock block 51 to prevent flow of flushing fluid proximally of the O-ring 83.

At least one and as shown in FIGS. 6 and 7 first or left stylet 146 and second or right stylet 147 are disposed within respective first or left guide cannula 148 and second or right guide cannula 149 carried by handle 23 for slidable disposition within passageway 39 of sheath 22. More specifically, guide cannulas 148 and 149 are slidably mounted in side by side disposition in lower portion 39b of bore 48 adjacent and below optical element 27. The guide cannulas are fastened together by any suitable means such as solder 151. Left and right guide cannulas 148 and 149 are identical in structure and each include an outer guide tube 152 made from a suitable material such as stainless steel having outside and inside diameters of approximately 0.072 and 0.062 inch and a length of approximately 10.5 inches. Guide tubes 152 are provided with proximal and distal extremities 153 and 154 and a central passage or lumen 155 extending between extremities 153 and 154. Proximal extremities 153 are each provided with a flange 156.

A plurality of circumferentially-extending T-shaped slots 157 are longitudinally spaced-apart along distalmost portion 154a of distal extremity 154 of each guide tube 152 for adding flexibility to flexible portion 154a (see FIG. 8). Each slot 157 subtends an angle less than 360° and has a transverse portion 157a with a suitable width ranging from approximately 0.012 to 0.016 inch. Slots 157 are not offset radially and therefore provide a backbone or rib 161 extending longitudinally of guide tube 152. Rib 161 has a width in the proximalmost slot 157 ranging from 0.012 to 0.016 inch and tapers in width as it extends distally to a width at the distalmost slot ranging from approximately 0.007 to 0.011 inch.

Flanges 156 are included within the means of electrosurgical catheter 21 for securing left and right guide cannulas 148 and 149 to handle 23. As illustrated in FIG. 1, handle shells 61 are formed with an internal cavity 166 and a passage 167 which extends from cavity 166 to an opening adjacent socket 67. The proximalmost portion of guide tube proximal extremities 153 are disposed within passage 167 and the passage includes an enlarged portion 168 which is sized and shaped to snugly receive flanges 156 so as to restrict longitudinal movement of the guide tube cannulas 148 and 149 within passage 167. Guide tubes 152 can be secured within passage 167 by any suitable means such as an adhesive (not shown). The passage 167 is aligned so that left and right guide cannulas 148 and 149 extend outwardly from handle 23 and distally through lower portion 48b of hub bore 48 into lower portion 39b of tube passageway 39 when sheath 22 is mounted to handle 23. Guide tubes 152 have a length so that distalmost portions 154a extend beyond tube opening 41 and viewing face 28 of endoscope 26.

Distal extremity 36b of tube 36 is provided with a cutout 171 for forming tube opening 41 and an elongate tube extension 172 from tube outer or sidewall 38 (see FIGS. 2, 7 and 8). Cutout 171 causes upper portion 39a of tube passageway 39 to terminate at opening 41. Tube extension 172, which is generally U-shaped in crosssection as shown in FIG. 7, is formed with spaced-apart flared side portions 173 which serve to receive and support distalmost portions 154a of guide tubes 152. Extension 172 has a length greater than that of distalmost portions 154a so that left and right guide cannulas 148 and 149 do not extend longitudinally beyond the tube extension 172.

Means for actuating the bending and/or straightening of distalmost portion 154a of each guide tube 152 includes an elongate actuation element or ribbon 176 made from any suitable materials such as stainless steel and having proximal and distal end portions 176a and 176b. Substantially rigid ribbon 176 has a cross-section which inhibits bending of the ribbon when placed under axial compression. It is preferable that ribbon 176 has a cross-sectional configuration with a width W greater than its thickness T. In the embodiment of ribbon 176 illustrated in FIG. 6, the ribbon is generally planar so as to be a strip and has a width of approximately 0.030 inch and a thickness of approximately 0.007 inch.

Ribbon 176 is relatively snugly disposed or sandwiched between the inside of guide tube 152 and the respective stylet 146 and 147 carried therein so as to further inhibit bending of the ribbon when placed under compression. Distal end portion 176b of ribbon 176 is secured to the inside of guide tube 152 distally of portion 154a by any suitable means such as solder 177 (see FIG. 9). Ribbon 176 is attached to the inside of the guide tube in diametric opposition to rib 161 and stretches the length of the guide tube 152. Each ribbon 176 extends from proximal extremity 153 of the respective guide tube into internal cavity 166 of handle 23 where the ribbons connect to an actuation or lever assembly 181.

Lever assembly 181, illustrated in FIG. 1, serves to simultaneously move first and second ribbons 176 proximally and distally within respective left and right guide cannulas 148 and 149. The lever assembly 181 includes a rod or shaft 182 made from a suitable material such as stainless steel and rotatably mounted within a bore 183 extending transversely through handle 23. Shaft 182 is provided with a bore-like recess 186 extending longitudinally along the outside thereof for receiving a stainless steel pin 187 to which the proximal end portions 176b of first and second ribbons 176 are spot welded or otherwise suitably secured in spaced-apart disposition. A plastic U-shaped lever element or lever 191 extends over the top of coupling portion 63 and is secured to each end of pivot shaft 182. Lever 191 has a transversely-extending portion 191a which travels within a cutout 192 provided at the top of coupling portion 63 above socket 67 and the coupling portion is further provided with a plurality of transversely-extending generally parallel spaced-apart detents 193 for indexing the lever 191 as it travels proximally and distally through cutout 192.

Lever 191 rotates through an angle of approximately 45° as it pivots about the axis of shaft 182 from a first position shown in solid lines in FIG. 1 in which distalmost portions 154a are generally straight and a second position shown in phantom lines in FIG. 1 in which distalmost portions 154a are fully bent as shown in phantom lines in FIGS. 1 and 8. Shaft 182 is circumferentially sized so that 45° rotation of the shaft causes ribbons 176 to bend distalmost portions 154a of guide tubes 152 through an angle of approximately 0° to 90°. Detents 193 can be positioned to correspond with particularly desirable angles within this range. Ribbons 176 are circumferentially placed on guide tubes 152 so that left and right guide cannulas 148 and 149 bend apart at an angle of approximately 40° (see FIG. 7). Although the disclosed and illustrated lever assembly 181 causes distalmost portions 154a of guide cannulas 148 and 149 to always bend together, it should be appreciated that lever assembly could be segmented to permit individual bending of the distal ends of the guide cannulas and be within the scope of the present invention.

The elongate actuation elements or ribbons for articulating left and right guide cannulas 148 and 149 can have other rigidity enhancing configurations for permitting their use under compressive forces and be within the scope of the present invention. For example, an elongate actuation element such as actuation element 201 illustrated in FIG. 10 could be utilized. Actuation element 201 has a cross-sectional which is arcuate in shape. The curvature of actuation element 201 adds to the buckling strength of the ribbon.

A tubular actuation element can also be provided. For example, a tubular actuation element or tube 206 made from any suitable material such as stainless steel can be provided as illustrated in FIGS. 11 and 12. Actuation tube 206 is transversely sized so as to concentrically extend around the stylet within the guide tube 152 and has a distal extremity 207 with an outside diameter of approximately 0.059 inch and an inside diameter of approximately 0.052 inch. Distal extremity 207 is provided with a plurality of circumferentially-extending T-shaped slots 208 substantially similar to T-shaped slots 157 and longitudinally spaced apart along the distalmost portion 211 of actuation tube distal extremity 207 at approximately equal distances. Slots 208 are not offset radially about the longitudinal axis of actuation tube 206 and therefore provide a backbone or rib 212 extending longitudinally along the actuation tube 206. Rib 212 can have a constant width or be tapered as it extends distally in a manner similar to rib 161 of guide tube 152. Actuation tube 206 is angularly aligned within guide tube 152 so that its rib 212 is diametrically opposed to rib 161 of guide tube 152. The number of T-shaped slots 208 in actuation element 206 does not necessarily have to conform to the number of T-shaped slots 157 in guide tube 152 although in the embodiment of electrosurgical catheter 21 illustrated in FIG. 11, the number of T-shaped slots 157 and 208 are equal.

In yet another alternative embodiment of the elongate actuation element of the present invention, a tubular actuation member or tube 216 is provided which is substantially similar in composition and size to actuation tube 206. Actuation tube 216, illustrated in side elevational plan in FIG. 13, has a distal extremity 217 provided with an elongate cutout 218 which forms a linear rib 219 extending longitudinally of the actuation tube 216. Rib 219 has a width substantially the same as rib 212 of actuation tube 206 and an actuation tube 216 is angularly aligned within each guide tube 152 around the stylet therein so that rib 219 is aligned with and generally extends over rib 161 of the guide tube 152.

Actuation tubes 206 and 216 are each secured to the guide tube 152 and actuated in substantially the same manner. In this regard, an actuation tube 206 or 216 is secured at its distal end to the end of each guide tube 152 distal of T-shaped slots 157. The actuation tubes 206 and 216 have respective proximal extremities (not shown) which are substantially similar to rib 161. These proximal extremities are secured to lever assembly 181 in the same manner as rib 161 for bending and straightening of the guide tubes 152.

Left and right stylets 146 and 147 are substantially identical in construction and each include a flexible elongate radio frequency electrode 226 formed from a suitable conductive material such as a nickel titanium alloy having superelastic properties so that the needle electrode returns to its original configuration after being bent as hereinafter described. Each needle electrode 226 has a proximal extremity 226a and a distal extremity 226b with a sharpened distal tip 227. Electrodes 226 each have an external diameter of approximately 0.018 inch.

A flexible tube member or sleeve 231 made from any suitable insulating material such as nylon is coaxially carried about each needle electrode 226. Each insulating sleeve 231 has a proximal extremity 231a and a distal extremity 231b and is formed with first and second passageways or lumens 232 and 233 which extend longitudinally the length thereof. Second lumen 233 is closed at its distal end. Insulating sleeves 231 are each oval-shaped in cross-section and each have outer transverse dimensions of approximately 0.010 by 0.034 inch. First lumens 232 each have an inner diameter of approximately 0.021 inch.

First and second elongate tubular members or control tubes 236 serve to couple first and second insulating sleeves 231 and internally carry first and second needle electrodes 226 to handle 23 of electrosurgical catheter 21. Control tubes 236 are each made from any suitable material such as stainless steel and have proximal and distal extremities 236a and 236b. A central bore 237 extends longitudinally the length of each control tube 236. Each control tube 236 is externally sized to fit within first lumen 232 of the respective sleeve 231 and extends substantially the entire length of the sleeve for adding compressive or buckling strength to the sleeve. The insulating sleeve 231 is stretched and annealed so as to shrink about the control tube 236 and thus secure the insulating sleeve to the control tube. Each sleeve 231 is longitudinally sized so that it precludes electrical contact between the respective control tube 236 and guide cannula 148 or 149 at all times.

First and second temperature sensing or sensor means in the form of first and second thermocouples 241 and 242 are carried by the distal extremity 231b of each insulating sleeve 231. First and second thermocouples 241 and 242 are each disposed within second lumen 233 respective distances of approximately one millimeter and six millimeters from the distal end of the insulating sleeve. Two first leads 243 are electrically connected to first thermocouple 241 and two second leads 244 are electrically connected to second thermocouple 242. First and second leads 243 and 244 extend through second lumen 233 the length of the insulating sleeve 231 to proximal extremity 231a thereof.

Operative means in the form of first or left actuation assembly 251 and second or right actuation assembly 252 is carried by sheath 22 and included within handle 23 for causing respective left and right stylets 146 and 147 to move distally and proximally within respective left and right guide canulas 148 and 149 (see FIGS. 1 and 14–16). Actuation assemblies 251 and 252 are aligned side by side within cavity 166 of handle shell 61 and each pivot when engaged with a shaft element or shaft 253 disposed substantially perpendicular to the actuation assemblies and extending transversely through handle depending portion 64 perpendicular to longitudinal axis 37. Left actuation assembly 251 includes a first or left needle electrode and insulating sleeve drive element 256 and right actuation assembly 252 includes a second or right needle electrode and insulating sleeve drive element 257. Drive elements 256 and 257 are each generally planar in confirmation and made from any suitable material such as polycarbonate. The drive elements 256 and 257 are substantially identical in structure and operation except that left drive element 256 is provided with a finger actuation element or lever 258 which extends from cavity 166 through an opening 259 in shell 61.

Drive elements 256 and 257 are provided with transversely aligned bores 261 for receiving pivot shaft 253. Each of bores 261 is square in cross-section, as illustrated in FIG. 16 with respect to right actuation assembly 252. Shaft 253 has an opposite first or left end portion 253a and a second or right end portion 253b which are each circular in cross-section and rotatably received within transversely aligned bores 262 in left and right shell side portions 61a and 61b (see FIG. 14). Shaft 253 is longitudinally sized so as to extend beyond the outside of right side portion 61b at all times and a lever 266 is rotatably mounted about shaft right end portion 253b.

Means which includes shaft 253 is included within electrosurgical catheter 21 for selectively engaging and disengaging right actuation assembly 252. Shaft 253 is further provided with a first or left torque transmitting portion 253c and a second or right torque transmitting portion 253d which are each square in cross-section, as illustrated in FIGS. 14 and 16 with respect to right square portion 253d, and a central portion 253e which is circular in cross-section and thus similar to end portions 253a and 253b.

Shaft 253 is movable longitudinally between a first or fully engaged position illustrated in FIG. 14 in which right square portion 253d is disposed within bore 261 in right drive element 257 and a second or partially engaged position, not illustrated, in which right square portion 253d has been moved out of the bore 261 in right drive element 257 into a central space between the drive elements 256 and 257. Left square portion 253c is longitudinally sized so as to remain within bore 261 of left drive element 256 when shaft 253 is in each of its first and second positions. Shaft 253 and bore 267 in lever 266 are longitudinally sized so that shaft right end portion 253a extends into the lever 267 in each of its first and second positions. The shaft 253 is further provided with an integral longitudinally-extending left pin 271 having a plastic cover or cap 272 secured thereto for manually moving the shaft to its fully engaged position and a similar right pin 273 having a plastic cover or cap 274 secured thereto for manually moving the shaft to its partially engaged position. Travel of shaft 253 is limited by the engagement of caps 272 and 274 with handle shell 61. Thus, right actuation assembly 252 can be engaged or disengaged relative to left actuation assembly 251 by merely moving shaft 253 between its fully engaged and partially engaged positions.

Each of actuation assemblies 251 and 252 includes means for securing proximal extremity 226a of the respective needle electrode 226 thereto so that the needle electrode moves longitudinally within guide tube 152 as respective drive element 256 or 257 rotates with shaft 253. As illustrated in FIG. 1 with respect to left actuation assembly 251, each drive element 256 and 257 includes a retainer 276 formed integral therewith. Retainer 276 includes a recess 277 for cooperatively receiving and securing an enlarged connector 278 electrically coupled and secured to the proximal end of the needle electrode 226. Connector 278 is mounted within recess 277 to move with the drive element about the axis of shaft 253.

Means is provided for pivotly coupling each of the insulating sleeves 231 to its respective drive element 256 or 257 and includes an insulating sleeve return element or hood 281 made from any suitable material such as polycarbonate (see FIGS. 1, 14 and 15). Each hood 281 is generally U-shaped in conformation and is formed with spaced-apart first and second sidewalls 282 interconnected by an arcuately-extending outer wall 283 as shown in FIG. 14. Sidewalls 282 and outer wall 283 form an inner space 284. The hood is pivotally connected to the drive element by a pin 286 so that a portion of the drive element extends inside of the hood 281. A transversely extending recess 287 is provided at the outer rear portion of arcuate outer wall 283 and is sized so as to cooperatively receive a rod-like member 291 secured to the proximal end of the respective control tube 236. Rod member 291 is made from any suitable material such as stainless steel and is secured to the control tube by a suitable means such as soldering. A bore 292 extends diametrically through rod member 291 and communicates with bore 237 of the control tube. Proximal extremity 226a of the respective needle electrode 226 slidably extends from control tube bore 237 through rod member bore 292. Thus, pivoting of hood 281 about pin 286 causes the insulating sleeve 231 carried by the control tube 236 to move longitudinally relative to the respective needle electrode 226.

Relative movement between a drive element 256 or 257 and handle shell 61 and between a hood 281 and its respective drive element 256 or 257 can now be described with respect to left actuation assembly 251 illustrated in side elevational plan in FIG. 1. Left drive element 256 is movable between a first or home position shown in solid lines in FIG. 1 and a second or actuated position (not shown) to which the drive element would pivot about shaft 253 in the direction identified by reference numeral 288 in FIG. 1. When the left drive element 256 is in its illustrated home position, left needle electrode 226 is fully retracted within left guide cannula 148. When the left drive element 256 is in its fully actuated or counterclockwise most position, the needle electrode 226 extends from left guide cannula 148 a predetermined distance ranging from 10 to 22 millimeters.

Left hood 281 is rotatable about pin 286 between a first or extended position, shown in solid lines in FIG. 1, and a second or retracted position (not shown). Clockwise rotation of hood 281 relative to left drive element 256 is limited by the engagement of internal stop 296 extending inwardly from one of sidewalls 282 into inner space 284 with forward surface 297 of the drive element or the earlier engagement of hood outer wall 283 with stop 298 formed integral with handle shell 61.

Each hood 281 is biased toward its retracted position by a coil spring 303 disposed within a recess 304 in the drive element and secured at one end to a hook 307 formed on the drive element 256 and at the other end to a retaining pin 308 extending transversely through inner space 284 and connected at its ends to spaced-apart side walls 282 (see FIGS. 1 and 15). An arcuately shaped opening 309 is formed in drive element 256 and extends into recess 304 to permit travel of the retaining pin 308 as hood 281 moves between its two positions.

Means is provided for retaining each hood 281 in its extended position under the force of coil spring 303 and includes a flexible stop 316 formed integral with one of thin sidewalls 282 by means of a U-shaped opening 316 formed in the sidewall (see FIG. 1). Flexible stop 317, as illustrated in FIG. 15 with respect to left actuation assembly 251, includes a hinge 318 and an extension 321 formed with a forward surface 322 extending inwardly from the outer surface of sidewall 282 at an approximately right angle and a ramped surface 323 extending at an oblique angle from the inner surface of the sidewall to join the protruding end of forward surface 322. The drive element 256 is provided with a first cutout 326 which terminates at a limit wall 327 projecting outwardly from the drive element at an approximately right angle. Extension 321 extends into first cutout 326 and the engagement of forward surface 322 of stop 316 with limit wall 327 restricts clockwise rotation of the hood 281 relative to the left drive element 256.

A U-shaped plunger element or plunger 331 made from plastic or any other suitable material is included with each of actuation assemblies 251 and 252 and is included within the means for releasing and unlocking hood 281 to permit the hood to move to its retracted position. As illustrated in FIG. 1, 14 and 15, plunger 331 is formed with spaced-apart, parallel guide portions 332 and engagement wall 333 extending therebetween. The front portion of the drive element 256 or 257 is formed with a second opposite cutout 336 opposite first cutout 326. The cutouts 326 and 336 cooperatively receive guide portions 332 and form a central rail 337 which extends between the guide portions 332. A slot 338 extends through central rail 337, as illustrated in FIG. 14, and an elongate coil spring 341 is disposed within slot 338 for biasing plunger 331 away from limit wall 327 (see FIG. 15). Relative movement between plunger 331 and central rail 337 against the force of coil spring 341 causes one of guide portions 332 to engage ramped surface 323 of flexible stop 316. Further movement of the plunger 331 along ramped surface 323 causes flexible stop 316 to pivot outwardly at hinge 318 and thus cause extension 321 to disengage from limit wall 327. The ultimate engagement of plunger 331 with limit wall 327 precludes further actuation of the drive element.

Adjustable means is provided for engaging the U-shaped plungers 331 as actuation assemblies 251 and/or 252 are pivoted upwardly in cavity 166 about the axis of shaft 253. This adjustment means includes a generally rod-like cross member 346 made from plastic or any other suitable material extending transversely through internal cavity 166 of shell 61 (see FIG. 14). Left and right shell side portions 61a and 61b are provided with aligned arcuately-extending first and second slots 347 for receiving the ends of cross member 346 and causing plunger 331 to engage the cross member 346 as the respective drive element is actuated (see FIG. 1). Slots 347 are shaped and positioned on shell 61 so that the release point of hood 281 during the actuation of one or both of drive elements 256 and 257 can be adjusted. Cross member 346 is provided with end caps 348 on each end for retaining the cross member within slots 347 and facilitating adjustment of the cross member relative to graduations (not shown) which can be provided on the outside of shell 61. Engagement wall 333 of each U-shaped plunger 331 is provided with an inclined outer surface 349. When the plunger 331 engages cross member 346 the resultant force exerted on the cross member 346 by the inclined surface 359 is in a direction generally perpendicular to the direction of arcuate slots 347. In this manner, drift of the cross member through slots 347 is minimized if not eliminated.

Lever 266 is included within the means of handle 23 for adjusting the position of cross member 346 in slots 347 (see FIG. 14). Lever 266 is formed with an integral extension 351 which extends through a slot 352 provided in shell right side portion 61b (see FIG. 16). Slot 352 is generally arcuate in shape and extends around a portion of the bore 262 in right side portion 61b. Cross member 346 is formed with an integral flexible tail 353 depending at an approximately right angle from the center thereof between left and right actuator assemblies 251 and 252 (see FIGS. 1 and 14). Tail 353 includes an end portion 353a which wraps partially around the center of shaft 253 and is formed with a C-shaped clasp 354 which snaps around the end of extension 351. Thus, movement of extension 351 downwardly through slot 352 by the rotation of lever 266 about shaft 253 pulls cross member 346 downwardly in arcuate slots 347.

A cable 361 terminating in a connector 362 is removably connected to a printed circuit board 363 carried within shell cavity 166 at the bottom of handle 23 for permitting electrical connections between left and right needle electrodes 222 and first and second thermocouples 241 and 242 carried by each of left and right stylets 146 and 147. Electrosurgical catheter 21 can be provided a microchip 364 on printed circuit board 363 for monitoring the usage of electrosurgical catheter 21. Microchip 364 can, for example, be of the type which measures the time during which radio frequency energy is passing through needle electrodes 226 and which renders the catheter electrically or otherwise unusable after the catheter usage reaches a predetermined level. Wires 366 serve to electrically connect proximal extremities 226a of needle electrodes 226 with circuit board 363 and additional wires (not shown) serve to electrically connect first and second leads 243 and 244 from thermocouples 241 and 242 to the circuit board 363. Cable 361 and connecter 362 permit electrosurgical catheter 21 to be used with a conventional radio frequency generator and controller 367 as illustrated in FIG. 1.

Left and right side portions 61a and 61b of handle shell 61 are formed with an opening 368 at the bottom of depending portion 64 which is sized and shaped to receive a finger such as the thumb of a human hand. Opening 368 and finger lever 258 serve to form scissortype grip on electrosurgical catheter 21.

Handle 23 of electrosurgical catheter 21 includes removable additional or second adapter means in the form of first plug 371 for adapting electrosurgical catheter 21 for use with a second conventional endoscope as illustrated in FIG. 17. First plug 371 mounts to coupling portion 63 of the handle 23 and is formed with a body 372 which is sized and shaped to snugly fit within distal part 373 of internal recess 71 (see FIGS. 17, 18 and 20). Body 372, when viewed in cross-section as in FIG. 18, has a rounded top portion 372a and a squared-off or tab 374 depends from the center of body 372 and flares outwardly from bottom portion 372b to facilitate its grasping by the fingers of a human hand. Cooperative mating means is carried by body 372 and handle proximal section 68 and includes opposed first channels 376 formed on the bottom portion of sidewall 74 along the inside adjacent internal wall 72 (see FIGS. 17 and 20). Channels 376 extend in directions perpendicular to longitudinal axis 37. Oppositely extending ridges 377 are formed along bottom portion 372b for slidably engaging first channels 376 when first plug 371 is pushed upwardly into distal part 373 of internal recess 71 adjacent internal wall 72.

First plug 371 is longitudinally sized and provided with suitable cooperative mating means for permitting catheter 21 to be used with a conventional rod lens endoscope 381 of the type manufactured by Circon ACMI. Endoscope 381, a portion of which is shown in FIG. 17, includes an optical element 382 with a distal viewing face (not shown). Optical element 382 is connected to a lens housing 383 having an eyepiece 384 by a fitting 386 provided with a light post 387. Fitting 386 includes a conventional coupling extension 388. Plug 371 is provided with a longitudinally-extending bore 391 through bottom portion 372b for receiving optical element 382 of endoscope 381 and a recess in the form of channel 392 extending along the bottom of a portion of bore 391 for snugly receiving coupling extension 388 (see FIG. 18). Plug 371 is longitudinally sized and shaped so that endoscope fitting 386 abuts the plug 371 when optical element 382 extends through bore 391 into lower portion 39b of sheath passageway 39 and the viewing face of optical element 382 is disposed adjacent passageway opening 41 in substantially the same position as illustrated in FIG. 1 with respect to viewing face 28 of endoscope 26. The snug disposition of coupling extension 388 in channel 392 restricts rotation of endoscope 381 about longitudinal axis 37. Endoscope 381 is secured within sheath 22 by locking assembly 46 in the same manner as discussed above with respect to endoscope 26.

Third or additional adapter means in the form of second plug 401 is included within coupling portion 63 of electrosurgical catheter 21 for permitting the catheter to be used with yet other conventional endoscopes. Second plug 401, which is illustrated in FIGS. 19–22, has a cross-sectional shape similar to first plug 371 and includes a body 402 having a rounded or dome-like top portion 402a and a squared-off bottom portion 402b. A tab 403 similar to tab 374 of first plug 371 depends from the center of bottom portion 402b of the body 402. Second plug 401 has a size and shape to permit its insertion into proximal part 406 of internal recess 71. Additional cooperative mating means is carried by proximal section 68 and plug 401 for removably securing the plug within proximal part 406. In this regard, proximal section 68 is provided with opposed second channels 407 which are substantially similar to first channels 376. Oppositely extending elongate protuberances or ridges 408 substantially similar to ridges 377 are formed on each side of bottom portion 372b for snug disposition within channels 407.

Plug body 402 is provided with a central bore 411 opening into an enlarged recess 412 illustrated in crosssection in FIG. 21. As shown therein, enlarged recess 412 is formed from spaced-apart generally parallel opposed first and second side surfaces 413 and arcuately extending opposed top and bottom surfaces 414 so as to be generally elongate or oblong in cross-sectional shape. A ridge 416 projects upwardly from the center of bottom surface 414 and extends along the length of enlarged recess 412.

Second plug 401 permits electrosurgical catheter 21 to be used with a conventional endoscope 421 such as the type manufactured by Wolf. Endoscope 421, a portion of which is shown in FIG. 19, includes an elongate longitudinally-extending optical element 422 having a distal extremity with a viewing face (not shown) and a proximal extremity mounted to a fitting 423. A coupling extension 426 extends distally from fitting 423 and a light post 427 extends from the fitting at an approximate right angle. A lens housing 428 with an eyepiece 429 is connected to fitting 423 and forms the proximal portion of endoscope 421. Second plug 401 is longitudinally sized so that when fitting 423 abuts the second plug 401 and optical element 422 extends through central bore 411, first plug 371 and sheath 22, the distal viewing face of the optical element 422 is positioned adjacent sheath distal opening 41 similar to viewing face 28 of endoscope 26 as illustrated in FIGS. 1 and 8. Enlarged recess 412 is configured to receive coupling extension 426 of endoscope 421 and has a crosssectional shape which generally corresponds to the crosssectional shape of the coupling extension 426 so that endoscope 421 is precluded from rotating about longitudinal axis 37 of electrosurgical catheter 21. Locking assembly 46 serves to secure endoscope 421 within electrosurgical catheter 21.

Second plug 401 further permits electrosurgical catheter 21 to be utilized with a conventional endoscope 436 of the type manufactured by Karl Storz of Germany (see FIG. 22). Endoscope 436 is substantially similar to endoscope 421 and includes an elongate of rod-lens 437 extending from a fitting (not shown) and an optical element (not shown) projecting distally from the fitting. A coupling extension 438 extends distally from the fitting. Second plug 401 is formed with generally rectangular-shaped cutouts 441 which open onto side surfaces 413 and the proximal surface of plug 401. When endoscope 436 is mounted to electrosurgical catheter 21, its fitting generally abuts second plug 401 in the same manner as fitting 423 of endoscope 421 shown in FIGS. 19 and 20 and rod lens 437 extends through central bore 411 of the second plug 401, through first plug 371 and through upper portion 39a of sheath passageway 39. Actuation of locking assembly 46 serves to secure endoscope 436 to the catheter 21.

Second plug 401 is longitudinally sized so that the second plug, together with first plug 371, causes the distal viewing face of endoscope 436 to extend through passageway 39 to a point adjacent opening 41 in a manner similar to that illustrated in FIGS. 1 and 8 with respect to endoscope 26. Coupling extension 438 is snugly received within enlarged recess 412. Cutouts 441 of the enlarged recess 412 and central ridge 416 are included within the additional or second cooperative mating means of second plug 401 for precluding endoscope 436 from rotating about longitudinal axis 37 of electrosurgical catheter 21.

In operation and use, adjustable electrosurgical cartridge (AEC) or handle 23 of the present invention can be used for performing an electrosurgical procedure on tissue at a treatment site within a human body. Handle 23 is mounted to sheath 22 by inserting left and right guide cannulas 148 and 149 carrying left and right stylets 146 and 147 through lower portion 48b of hub bore 48 so that the guide canulas 148 and 149 extend down lower portion 39b of sheath passageway 39. As distal extremities 154 of left and right guide tubes 152 approach tube opening 41, optic lock block 51 is inserted into socket 67 of handle shell 61. When the block 51 is fully disposed within socket 61, distalmost portions 154a of guide tubes 152 are disposed within tube extension 172 beyond opening 141.

The operating physician selects one of four conventional endoscopes 26, 381, 421 or 436 and mounts the appropriate adapter plugs 371 and/or 401, if necessary, to proximal section 68 for use with the selected endoscope. The optical element of the endoscope is inserted through internal recess 71 and any plugs 371 and 401 disposed therein and then into sheath 22 so that the optical element extends through central bore 56 of optic lock block 51, upper portion 48a of hub bore 48 and upper portion 39a of tube passageway 39. Actuation of locking assembly 36 by rotation of optic lock collar 121 via radius bar 127 causes O-ring 83 to compress inwardly against the optical element and secure the optical element within block 51. Coupling portion 63 of handle 23 is precluded from separating from sheath 22 once the endoscope is so secured to sheath 22.

A suitable light source is connected to the light post of the endoscope and radio frequency generator and controller 367 is connected to cable 361. A source of a suitable flushing fluid such as a saline solution is coupled to first and second stopcocks 141 and 142 to permit introduction and/or withdrawal of a saline solution or other fluid through passageway 39 during the procedure.

Catheter sheath 22 is adapted for insertion into a natural body opening for performing a procedure. In one possible procedure, catheter 21 can be inserted into the urethral canal or urethra of a human male for performing an operation on the bladder. When inserting catheter 21 into the urethra, the operating physician grasps handle 23 by inserting his or her thumb through handle opening 368 and wrapping his or her other fingers around finger lever 258. While viewing through the endoscope, the operating physician can grasp the penis and insert tube distal extremity 36b into the urethra. Tube distal extremity 36b and tube extension 172 formed thereon are generally blunt so as to permit the tube 36 to easily pass through the urethra to the bladder without harming the urethral wall. The introduction of the flushing fluid through passageway 39 alongside the optical element and guide cannulas 148 and 149 facilitates viewing of the inside of the urethra and body during placement of tube distal extremity 36b therein.

Once electrosurgical catheter 21 has been properly positioned within the body, the operating physician can cause distalmost portions 154a of the guide tubes of left and right guide cannulas 148 and 149 to be bent to a desired angle between 0° and 90° relative to longitudinal axis 37 through movement of lever 191 of lever assembly 181. Detents 193 provided on the top of handle coupling portion 63 facilitate bending of the guide cannulas to the desired angle. T-shaped slots 157 provided in distalmost portion 154a of left and right guide tubes 152 permit relatively smooth bending of the guide tube. In the illustrated and described T-shaped slots 157, longitudinal portions 157b of the slots extend from each side of slot transverse portion 157a so as to more evenly distribute bending and minimize undesirable sharp edges extending into the central lumen or passage of the guide tubes. Any such sharp could snag the stylets slidably extending inside guide tubes 152.

Either one or both of left and right needle electrodes 226 can be extended from guide cannulas 148 and 149 for performing the electrosurgical procedure. In this regard, the operating physician positions shaft 253 so that either left actuation assembly 251 only or both left and right actuation assemblies 251 and 252 are in an engaged position. After the operating physician moves lever 266 to desirably positioned cross member 346 and has rotated catheter 21 about longitudinal axis 37 to a desired position in the urethra, the operating physician pulls on finger lever 258 to cause the engaged drive elements 256 and/or 257 to pivot with shaft 253 relative to handle 23. During this drive stroke, each engaged needle electrode 226 and associated insulating sleeve 231 moves distally through its guide tube 152 and exits distalmost portion 154a of the guide tube. The insulating sleeve is distanced approximately one millimeter behind the sharpened distal tip 227 of the needle electrode 226 prior to the engagement of plunger 331 with cross member 346. Full retraction of finger lever 258 causes the engaged needle electrode 226 to extend a predetermined distance ranging from 10 to 20 millimeters from the end of the guide tube 152.

The placement of cross member 346 within arcuate slots 347 determines when each engaged plunger 331 releases its associated flexible stop 316 so as to cause the hood 281 to pivot backwardly relative to the associated drive element and thus cause the insulating sleeve 231 of the engaged stylet to automatically retract relative to the associated needle electrode 226. The retractable pivoting of hood 281 relative to the associated drive element is limited by hood stop 296 engaging forward surface 297 of the drive element. Handle 23 is constructed so that the engagement of stop 296 and surface 297 results in distal extremity 231b of insulating sleeve 231 extending a predetermined distance of approximately six millimeters from the end of guide tube 152.

During the extension of left stylet 146 and/or right stylet 147 and during the procedure thereafter, tube extension 172 serves to support guide tube distalmost portions 154a against forces exerted against the stylets and guide cannulas 148 and 149 during the procedure. The bottom portion of tube extension 172 restricts distalmost portions 154a of the guide cannulas 148 and 149 from bending backwardly under these forces. Flared portions 173 of the tube extension 172 prevent the distalmost portions 154a from bending outwardly away from each other as the flared portions serve to cradle distal extremities 154a when distalmost portions 154a are in their bent or articulated positions. By so hindering movement of distalmost portions 154a from their known positions, catheter 21 permits more accurate placement of distal tips 227 of needle electrodes 226 during an electrosurgical procedure.

The unique placement of left and right guide cannulas 148 and 149 below the viewing face of the optical element permits greater visibility during the procedure because the distalmost portions 154a of guide tubes 152 do not generally obstruct the viewing region of the endoscope. As illustrated in FIGS. 1 and 8, viewing through endoscope 26 is particularly enhanced when the optical element of the endoscope is provided with a viewing face 28 which faces away from guide cannulas 148 and 149. The placement of distalmost portions 154a below the viewing face 28 permits the operating physician to view the bending of guide cannulas 148 and 149 and to easily observe the operating procedure performed by one or both of the needle electrodes 226 extending from the guide cannulas 148 and 149.

One or both needle electrodes 226 can be used during the electrosurgical procedure to perform single and/or dual coagulation. If only one needle electrode is extended, a conventional grounding element or pad must be placed against the patient to permit return of the radio frequency energy being supplied through the extended needle electrode 226. When both needle electrodes 226 are extended, monopolar coagulation can be performed by supplying radio frequency energy to either of the extended electrodes and utilizing the external pad as a ground return. Alternatively, bipolar coagulation can be performed by using one needle electrode as an energy supply electrode and the other needle electrode as a return or grounding electrode. As such, electrosurgical catheter 21 can be used for localized cutting, coagulation and dissection of tissue and is ideal for developing both small and large coagulative areas. First and second thermocouples 241 and 242 permit monitoring of the temperature in the tissue surrounding the targeted area of each needle electrode 226. Radio frequency generator and controller 367 is capable of providing both monopolar and bipolar radio frequency output at relatively low power of up to 50 watts.

Should left and right guide cannulas 148 and 149 need to be straightened partially or totally during the procedure, the relatively rigid push/pull ribbon or other actuation element carried within the guide cannulas 148 and 149 permits compressive forces to be exerted axially on the guide cannulas to straighten or extend their distalmost portions 154a.

Once the electrosurgical procedure has been completed inside of the body, finger lever 258 is moved away from opening 368 in the handle 23 so as to cause the extended stylets 146 and/or 147 to retract fully within respective guide cannulas 148 and 149. During this retraction stroke of actuation assemblies 251 and 252, stop 291 limits the pivoting of the engaged hood 281 about pin 286 thus causing the hood to return to its loaded position in which flexible stop 316 is in locked engagement with limit wall 327. The disengagement of plunger 331 with cross member 346 causes spring 341 to urge the plunger away from limit wall 327 thus permitting the flexible stop 316 to extend into first cutout 326. Lever 191 is moved to its distalmost position, shown in solid lines in FIG. 1, so that distalmost portions 154a of the guide tubes 152 are generally straightened as illustrated in FIGS. 1 and 8. The operating physician can now withdraw tube 36 from the urethra.

Sheath 22 and endoscope 26, once removed from handle 23, can be easily sterilized for reuse. In following procedures, another conventional rod lens endoscope such as one of endoscopes 26, 381, 421 or 436 can be easily utilized. In addition, a handle 23 can be selected in which needle electrodes 226 and actuation assemblies 251 and 252 have been sized so that the needle electrodes 226 extend from distal extremities 154a of guide tubes 152 a second and different predetermined distance within the previously described extension range. It should also be appreciated that a handle 23 can be provided in which the left and right needle electrodes 26 extend different distances from their respective guide tubes 152. For example, the left needle electrode 226 could extend from its guide tube 152 a distance less than the distance which the right needle electrode 226 extends from its guide tube.

Catheter 21 can also be used for performing a transurethral needle ablation procedure such as that described in copending U.S. patent application Serial No. 08/191,258 filed Feb. 2, 1994.

In another embodiment of the device or catheter of the present invention, an electrosurgical or needle ablation assembly 451 is shown in FIG. 23. Assembly 451 includes sheath means in the form of probe or sheath 452 which is adapted for use with a plurality of different scopes such as the conventional endoscope 26 of Olympus Corporation described above. As illustrated in FIGS. 23, 25 and 26, sheath 452 includes an elongate tubular member or tube 453 having proximal and distal extremities 453a and 453b. Substantially rigid tube 453 can be of any suitable type and size, as for example a 22 French catheter-like guide housing having a length of approximately 9 inches and being formed of stainless steel or any other suitable material. Tube 453 extends along a central longitudinal axis 454 and has an external or outer cylindrical wall 456 for forming an internal lumen or passageway 457 which extends from proximal extremity 453a to an opening 458 at distal extremity 453b. Passageway 457 is substantially similar in cross-section to passageway 39 of sheath 22 described above and, as shown in FIG. 28, includes an upper portion 457a and a lower portion 457b.

Tube distal extremity 453b is formed similar to distal extremity 36b of tube 36 and, in this regard, is provided with a cutout 461 along the upper portion of tube 453 for forming an elongate tube extension 462 with spaced apart side walls 463 and a generally rounded and depending distal end or tip 464. Each of the side walls 463, as shown most clearly in FIG. 26 with respect to the right wall 463, has a side profile similar to the drooping front end of a shoe. More specifically, each wall 463 has an elevated front wall portion 463a and a central flared wall portion 463b adjoining wall portion 463a proximally thereof. Front wall portion 463a extends upwardly at an approximately right angle from the bottom wall portion of tube wall 456 and is formed from a front surface 466 extending upwardly from end 464 and inclined rearwardly at an angle of approximately 45° relative to axis 454. A first arcuate surface 467 extends upwardly from front surface 466 before dipping downwardly to join a second arcuate surface 468 which extends further downwardly before curving upwardly to join the top of wall 456 at distal opening 458. Second arcuate surface 468 forms the top of flared wall portion 463b which, as shown in FIGS. 23 and 25, is inclined outwardly from the vertical at an angle ranging from approximately 15° to 25°.

A locking assembly 471 is mounted on proximal extremity 453a of tube 453 (see FIGS. 23, 24 and 27). Locking assembly 471 includes a generally conical-shaped housing or hub 472 made from stainless steel or any other suitable material. Housing 472 is truncated by a distal wall 473 which is secured to proximal extremity 453a of tube 453 by welding or any other suitable means. Hub 472 is further formed with a proximal cylindrical wall 476 and is provided with an internal recess or cavity 477 in communication with the open proximal end of hub 472. Cavity 477 is in communication with central passageway 457 of tube 453 by means of an opening 478 provided in distal wall 473.

Locking assembly 471 further includes a second annular member in the form of ring or optic lock collar 481 rotatably mounted about proximal cylindrical wall 476 of hub 472 between a first or unlocked position shown in phantom lines in FIG. 27 and a second or locked position shown in solid lines in FIG. 27. Lock collar 481 is made from stainless steel or any other suitable material and is provided with a central bore 482 which extends therethrough and is internally sized slightly larger than the external diameter of wall 476. Collar 481 is formed with a proximal flange 483 which extends inwardly in juxtaposition to the proximal end of hub 472. Flange 43 has first and second opposed lip portions 486 which extend inwardly beyond hub cylindrical wall 476 and have respective surfaces 487 which extend parallel to and face each other.

Means is provided for securing optic lock collar 481 to hub 472 and includes a circumferentially-extending slot 491 provided in proximal cylindrical wall 476. Slot 491 subtends an angle of approximately 60°. A radially-extending lever or radius bar 492 is mounted on optic lock collar 481. Radius bar 492 is provided with a threaded end portion 492a which extends through a threaded bore 493 provided in collar 481. End portion 492a extends inwardly beyond collar 481 into slot 491 so as to preclude lock collar 481 from sliding longitudinally off hub 472. The cooperative engagement of radius bar 492 and slot 491 further serves to limit the rotatable travel of optic lock collar 481 about hub 472 and thus defines the unlocked and locked positions of collar 481 described above.

First or left and second or right stopcocks 496 and 497 are provided on sheath 22 for permitting any suitable liquid such as a flushing fluid to be introduced into and withdrawn from sheath passageway 457. Stopcocks 496 and 497 are substantially similar to stopcocks 451 and 452 of device 21 described above and are attached to the opposite sides of hub 472 by any suitable means such as welding. First and second diametrically opposed bores 498 extend radially through hub 472 into internal cavity 477. Stopcocks 496 and 497 communicate with bores 498 and thus internal cavity 477.

Needle ablation assembly 451 further includes a transurethral needle ablation device 496 comprised of at least one and as shown in FIG. 23 a first or left guide cannula 507 and a second or right guide cannula 508 secured to handle means in the form of handle 511. Guide cannulas 507 and 508 are substantially similar to guide cannulas 148 and 149 described above. The guide cannulas 507 and 508 are identical in structure and are fastened together by any suitable means such as solder 512 (see FIG. 28). Each of the guide cannulas includes an outer guide tube 513 made from any suitable material such as stainless steel. Guide tubes 513 are provided with proximal and distal extremities 516 and 517 and a central passage or lumen 518 extending between extremities 516 and 517 (see FIGS. 26 and 33). Central lumen 518 terminates at an opening or port 519 at the distal end of guide tube 513. Guide cannulas 507 and 508 are adapted for slidable disposition within lower portion 457b of central passageway 457 of sheath 452 and, as such, each have outside and inside diameters of approximately 0.082 and 0.062 inch and a length of approximately 10 inches.

A plurality of circumferentially-extending L-shaped slots 526 are longitudinally spaced-apart along distalmost portion 517a of each guide tube 513 for providing flexibility to the distalmost or flexible portion 517a (see FIG. 26). Each slot 526 subtends an angle less than 360° and has a transverse portion 526a with a suitable width ranging from approximately 0.012 to 0.016 inch and a longitudinal portion 526b extending proximally from each end of transverse portion 26a a distance ranging from 0.020 to 0.040 inch and preferably approximately 0.032 inch. Slots 526 are not offset radially and therefore provide a backbone or rib 527 extending longitudinally of the guide tube 513. Rib has a height, as when view from the side as in FIG. 26, ranging from 0.005 to 0.015 inch and preferably approximately 0.008 inch.

Handle 511 is adapted for gripping by a human hand and includes an outer shell 531 made from a suitable material such as polycarbonate and formed from a first or left side portion 531a and a second or right-hand portion 531b as illustrated in FIG. 23. Handle shell 531 includes an upper portion 532 and a lower portion 533 and is hollow so as to have an internal cavity 534 therein.

An elongate tubular member in the form of articulation hub 537 is carried by upper portion 532 of the handle shell 531. Articulation hub 537 is made from polycarbonate or any other suitable material and includes a first or front portion 537a in the form of a truncated cone, a second or central portion 537b and a third or rear portion 537c which is disk-like and disposed traverse to the longitudinal axis of the hub 537. A central bore 538 extends longitudinally through front, central and rear portions 537a, 537b and 537c of the articulation hub. Shell handle portions 531a and 531b are formed with aligned front cutouts 541 and aligned rear cutouts 542 for receiving articulation of 537 so that the front portion 537a of the articulation hub extends distally of handle upper portion 532 and rear portion 537c of the articulation hub extends proximally of handle upper portion 532. Articulation hub 537 and cutouts 541 and 542 are cooperatively sized and shaped so as to restrict the articulation hub from rotating about its longitudinal axis relative to handle shell 531. Means is carried by guide cannulas 507 and 508 and handle shell 531 for attaching the guide cannulas to handle 511 (see FIGS. 24 and 27). In this regard, front portion 537a of articulation hub 537 is formed with first and second spaced-apart parallel grooves 543 which extend along the bottom of portion 537a for receiving proximal extremities 516 of cannula guide tubes 513. A retention element in the form of retention block 546 is disposed on the underside of front portion 537a for retaining guide tubes 513 against the bottom of articulation hub 537. Retention block 546 is made from polycarbonate or any other suitable material and is provided with first and second spaced-apart grooves 547 on the top thereof for receiving the guide tubes 513. A strap-like loop or band 548 is formed integral with retention block 546 and slips over the top of the front portion 537a for attaching block 546 to articulation hub 537. Band 548 includes a flange 549 extending inwardly along the inner periphery thereof which seats within a proximal groove 551 extending around the top and sides of front portion 537a.

Left and right guide cannulas 507 and 508, as so attached to handle 511, are adapted for slidable disposition within lower portion 457b of sheath passageway 457 (see FIGS. 24 and 28). Guide cannulas 507 and 508 are mounted in side by side disposition in passageway 457 and extend distally of articulation hub 537 a distance of approximately 9 inches so that flexible portions 517a of guide tubes 513 are generally disposed within elongate tube extension 462 distal of opening 458.

Hub front portion 537a is seated within internal cavity 477 of hub 472 when guide cannulas 507 and 508 are so mounted within sheath 452. Seal means in the form of elastomeric cap 552 is carried by front portion 537a for inhibiting any liquid within passageway 457 from flowing proximally through or around the articulation hub 537 (see FIG. 24). Cap 552 is made from any suitable elastomeric material such as silicone and has a radially enlarged distal portion which sealably engages the inside wall of hub 537 forming cavity 477. An inwardly extending annular flange 553 is provided at the proximal end of cap 552 for securing the cap to the articulation hub 537. Flange 553 seats within a distal groove 554 extending around the top and sides of hub front portion 537a distal of band 548. Seal cap 552 is provided with a first or lower opening 556 which extends therethrough and is sized and shaped to sealably receive first and second guide cannulas 507 and 508. The seal cap 552 is further provided with a second opening or bore 557 which has a cross-sectional shape corresponding to central bore 538 of articulation hub 537.

Front portion 537a of articulation hub 537 is provided with a pair of oppositely aligned enlargements or ears 561 and 562, as illustrated in FIGS. 24 and 27, which are included within means for securing transurethral needle ablation device 506 to sheath 452. Right ear 562 is larger than left ear 561 as it subtends a slightly larger angle about longitudinal axis 454 than left ear 561. Hub cavity 477 includes left and right recesses 563 and 564 which are sized and shaped to cooperatively receive sideways-extending ears 561 and 562 when the ears extend within hub 472 distal of lip portions 486 of optic lock collar 481. When optic lock collar 481 is in its first or unlocked position, lip portions 486 extend across the top and bottom of cavity 477 so as to permit ears 461 and 462 to pass therebetween into cavity 477. The different sized ears 461 and 462 preclude sheath 452 from being mounted in an upside down position relative to device 506. When optic lock collar 481 is rotated to its second or locked position, lip portions 46 move over the proximal surfaces of ears 461 and 462 so as to retain front portion 537a of articulation hub 537 within internal cavity 477 of sheath hub 472.

Means in the form of assembly 569 is provided in device 506 for actuating the bending and/or straightening of flexible portions 517a of guide tubes 513. An elongate actuation element or ribbon 571 substantially similar to ribbon 176 described above and made from stainless steel or any other suitable material is included in assembly 569. Actuation ribbon 571, shown in FIGS. 24, 26, 28 and 30, is generally U-shaped and has a proximal portion 571 consisting of the base of the U and first and second spaced-apart longitudinal extensions 572 having end portions which constitute distal portions 571b of the actuation ribbon. Each extension 572 is substantially planar and has a width of approximately 0.025 inch and a thickness of approximately 0.005 inch. As such, each extension 572 has a cross-section which inhibits bending in the plane thereof when the extension is placed under axial compression. Each of the extensions 572 extends longitudinally through a central lumen 518 of a guide tube 513, as illustrated in FIGS. 26 and 28, and the distal portion 571b thereof is secured by spot-weld 573 or any other suitable means to the end of the guide tube 513 distal of slots 526, as illustrated in FIG. 26. The proximal end of each extension 572 extends through a side port or window (not shown) provided in the top of the cylindrical wall of guide tube 513 inside handle shell 531. The strip-like proximal portion 571a of actuation ribbon 571 extends proximally therefrom along the planar bottom surface 574 of articulation hub central portion 537b (see FIGS. 29–31).

A strip-like leaf spring 576 made from spring steel or any other suitable material is juxtaposed below ribbon proximal portion 571a along hub central portion 537b (see FIGS. 24, 29 and 30). Ribbon 571 and leaf spring 576 are retained against bottom surface 574 at the distal end of hub central portion 537b by a U-shaped flexible clip 577 made from polycarbonate or any other suitable material. Forward clip 577 has first and second spaced-apart arms 578 which extend upwardly along each side of articulation hub 537. Arms 578 have opposed inwardly-extending extensions or ridges which extend over and engage the top of the articulation hub 537 for securing clip 577 thereto. Articulation hub 537 is formed with first and second spaced-apart transverse extensions 579 along both sides thereof for forming recesses 580 which receive clip arms 578 and restrict clip 577 from moving longitudinally along the articulation hub.

The actuation ribbon 571 and leaf spring 576 are provided with respective bores 581 and 582 at their respective proximal ends. A post 583 depending from bottom surface 574 and formed integral with the articulation hub 537 extends through bores 581 and 582. Ribbon 571 and leaf spring 576 are retained on post 583 by a clip 586 which is substantially similar to forward clip 577. Rear clip 586 has first and second spaced apart arms 587 which extend upwardly along the sides of articulation hub 537 and are formed with opposed ridges at the upper ends thereof which extend over the top edges of the articulation hub (see FIG. 29) for securing clip 586 thereto. Rear clip 586 is provided with a bore 588 which is sized and shaped to cooperatively receive post 583 when the clip 586 is so secured to articulation hub 537. Clip 586 thus retains ribbon 571 and spring 576 on post 583.

An outwardly-extending post 591 is provided on the upper end of each arm 578 of forward clip of 577 as illustrated in FIG. 30. Transversely-aligned posts 591 are disposed within cooperatively sized and shaped recesses 592 provided in handle shell portions 531a and 531b for further securing articulation hub 537 to handle 511. Similar posts 593 are provided on the outside of the upper ends of each arm 587 of rear clip 586 and, as illustrated in FIG. 30, are disposed within opposed recesses 594 provided in portions 531a and 531b of handle shell 531 for also securing hub 537 to handle 511.

Figure 33:
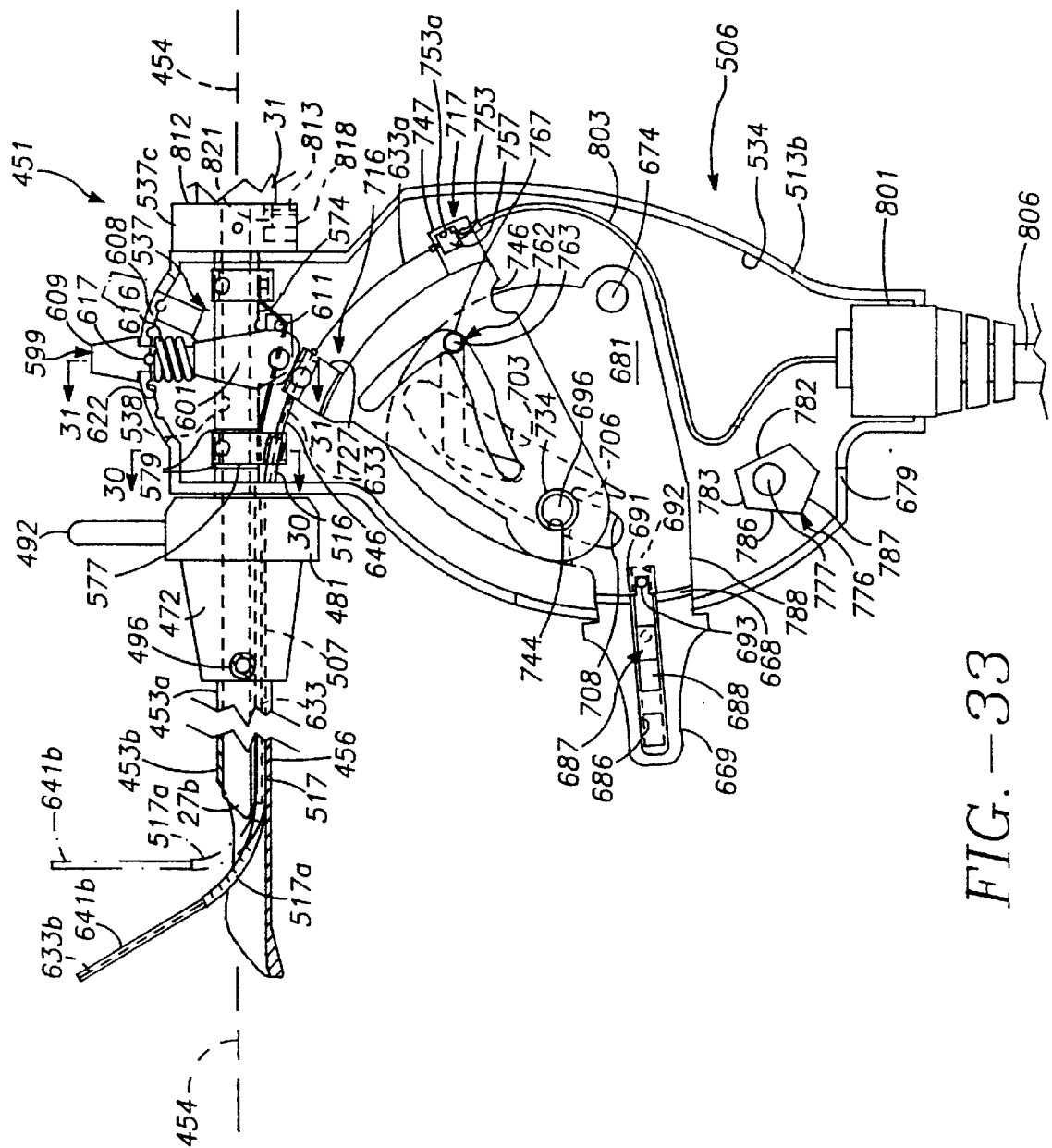
FIG. 33 is a segmented side elevational view, partially cross-sectioned and similar to FIG. 24, of the electrosurgical assembly of FIG. 23 in another position.

Forward clip 577 is provided with left and right grooves 596 and 597 extending longitudinally along the bottom thereof for further securing the proximal ends of left and right guide cannulas 507 and 508 to handle (see FIGS. 33 and 30). Grooves 596 and 597 are each formed with central enlarged portions or pockets 596a and 597a. Proximal extremities 516 of cannula guide tubes 513 are each provided with terminal enlargements in the form of flanges or collars 598 which snugly seat within pockets 596a and 597a. In this manner, guide cannulas 507 and 508 are secured against longitudinal movement relative to handle 511 and thus sheath 452.

Actuation lever assembly 569 further includes a lever member or lever 599 having first and second spaced-apart legs 601 which extend around opposite sides of hub central portion 537b (see FIGS. 24, 29 and 31). Articulation hub 537 is formed with integral first and second spaced-apart bosses 602 which depend along each side of actuation ribbon 571 and leaf spring 576.

Transversely aligned cylindrical pivot studs 603 extend outwardly from bosses 602 and are disposed within respective transverse bores 604 provided in lever legs 601. The upper ends of legs 601 join at a stem 606 which extends upwardly through an arcuately-extending slot 607 provided in the arcuately-extending upper wall 608 formed by handle side portions 531a and 531b. A lever tab 609 sized and shaped for grasping by the fingers of a human hand is included within lever 599 and is snapped onto to the top of stem 606. Lever tab 609 rides along the outside of upper wall 608.

Lever 599 is pivotable about studs 603 between a forward position in which the lever 599 is inclined forwardly relative to articulation hub 537, as shown in solid lines in FIG. 24, and a rear position in which the lever 599 is inclined rearwardly relative to the articulation hub, as shown in phantom lines in FIG. 24. A cylindrical pin 611 made from stainless steel or any other suitable material extends between the rear portions of legs 601 below bottom surface 574 and above actuation ribbon 571 and leaf spring 576 (see FIG. 35). The opposite ends of pin 611 are disposed within respective transversely-aligned bores 612 provided in legs 601. Bores 612 are positioned so that when the lever 599 is in its forward position, pin 611 generally abuts bottom surface 574 of articulation hub 537.

Actuation ribbon 571 is longitudinally sized such that when lever 599 is in its forward position, first and second guide cannulas 507 and 508 are in their at home position in which they are generally straight as shown in solid lines in FIGS. 24 and 26. As lever 599 is pivoted to its rearward position, pin 611 moves downwardly away from bottom surface 574. Pin 611 is spaced its maximum distance from bottom surface 574 when lever 599 is in its rearward position. The downward movement of pin 611 relative to articulation hub 537 lengthens the distance actuation ribbon 571 must extend between forward and rear clips 577 and 586 and thus pulls extensions 572 proximally within guide tubes 513. This pulling of actuation ribbons 571, in turn, causes flexible portions 517a of guide tubes 513 to bend at slots 526. As such, each flexible portion 517a moves from its generally straightened position shown in solid lines in FIG. 26 to various angled positions some of which are shown in phantom lines in FIG. 26 until the flexible portion 517a subtends an angle of approximately 90° relative to longitudinal axis 454 when lever 599 is in its rearwardmost position. Flexible portions 517a splay at an angle ranging from 30° to 50°, similar to the splaying of the distal ends of left and right guide cannulas 148 and 149 illustrated above in dashed lines in FIG. 7, when so bent by actuation lever assembly 569.

Leaf spring 576 provides some resistance to the pivotal movement of lever 599 and thus inhibits accidental movement of the lever and related guide cannulas 507 and 508 during a procedure. The leaf spring 576 also serves to urge pin 618 to its home position against bottom surface 574 when lever 599 is in its forward position. Pin 618, in turn, urges actuation ribbon 571 forwardly in guide cannulas 507 and 508 and thus assists in straightening cannula flexible portions 517a. The generally planar construction of ribbon extensions 572 and the sandwiching of extensions 572 between the tubular wall of guide tubes 513 and the stylets described below within the guide tubes inhibits bending and buckling of the actuation ribbon 571 when it is placed in compression.

Actuation lever assembly 569 includes means for indexing the pivotal movement of lever 599 relative to handle shell 531. In this regard, a compressible spring 616 is provided around stem 606 of lever 599 and a transversely-extending pin 617 is disposed within a longitudinally-extending slot 618 provided in stem 606 (see FIGS. 31 and 33). Pin 617 is longitudinally sized so that the ends thereof extend outwardly beyond the periphery of stem 606. The ends of the pin are disposed atop spring 616 and the spring thus serves to urge the pin away from pivot studs 603. A plurality of pairs of grooves or detents 622 are provided on the underside of wall 608 on either side of slot 607 for receiving pin 617 when lever 599 is in certain predetermined positions relative to handle shell 531.

At least one and as shown in FIGS. 24 and 28 a first or left stylet 631 and a second or right stylet 632 are provided in transurethral needle ablation device 506. Left stylet 631 is slidably carried within left guide cannula 507 and right stylet 632 is slidably carried within right guide cannula 508. Stylets 631 and 632 are substantially similar to stylets 146 and 147 described above and each include a flexible elongate radio frequency electrode 633 substantially similar to electrode 226 and having a proximal extremity 633a and a distal extremity 633b with a sharpened distal tip 636. Needle electrodes 633 each have an external diameter of approximately 0.018 inch. Insulating means in the form of a flexible tube member or sleeve 641 substantially similar to sleeve 231 is coaxially disposed and carried about each needle electrode 633. Each insulating sleeve 641 has proximal and distal extremities 641a and 641b and is formed with first and second passageways or lumens 642 and 643 substantially similar to lumens 232 and 233 described above. Oval-shaped insulating sleeves 641 each have outer transverse dimensions of approximately 0.010 inch by 0.034 inch. First lumens 642 each have an inner diameter of approximately 0.021 inch.

First and second elongate tubular members or control tubes 646 substantially similar to control tubes 236 serve to couple first and second insulating sleeves 641 to handle 511 and also serve to carry first and second needle electrodes 633 to the handle 511. Control tubes 646 each have proximal and distal extremities 646a and 646b and a central bore 647 extending between these extremities. Sleeves 641 are longitudinally sized so that they extend over a significant length of control tubes 646 and thus preclude electrical contact between the control tubes and guide cannulas 507 and 508 at all times.

First and second temperature sensing or sensor means in the form of first and second thermocouples 656 and 657 are carried by the distal extremity 641b of each insulating sleeve 641 (see FIG. 35). Thermocouples 656 and 657 are substantially similar to thermocouples 241 and 242 described above and are respectively disposed within second lumens 643 of the insulating sleeves 641. Each first thermocouple 656 is distanced approximately one millimeter from the distal end of the insulating sleeve 641, while each second thermocouple 657 is distanced approximately six millimeters from the distal end of the insulating sleeve. First thermocouple 656 includes a pair of first leads 658 and second thermocouple 657 includes a pair of second leads 659. Leads 658 and 659 are substantially similar to first and second leads 243 and 244 described above and extend through second lumen 643 and proximal extremity 641a of insulating sleeve 641.

Operative means in the form of trigger actuation assembly 661 including first or left actuation means or assembly 662 and second or right actuation means or assembly 663 is carried by sheath 452 for causing respective left and right stylets 631 and 632 to move distally and proximally within respective left and right guide cannulas 507 and 508 (see FIGS. 24 and 32–35). Actuation assemblies 662 and 663 are aligned side-by-side within cavity 534 of handle shell 531. Each of actuation assemblies 662 and 663 includes a primary drive element pivotally carried by handle shell 531. In this regard, left actuation assembly 662 has a first or left primary drive element 666 and right actuation assembly 663 has a second or right primary drive element 667. Drive elements 666 and 667 are each made from any suitable material such as polycarbonate.

Right drive element 667 serves as the master drive element for trigger assembly 661 and has a generally planar plate portion 668 formed integral with a lever portion or finger lever 669. Plate portion 668 is generally pie-shaped and has first and second opposite planar surfaces in the form of inner surface 671 and outer surface 672. A bore 673 extends through surfaces 671 and 672 at the apex of the pie-shaped portion 668 for snugly receiving a cylindrical pin 674 made from stainless steel or any other suitable material. The right end of primary pivot pin 674 is disposed within a bore 676 extending into the inside of handle right side portion 531b and the left end of the pin is disposed within a bore 677 extending into the inside of hand left side portion 531a (see FIG. 32). Bores 676 and 677 are provided toward the rear of handle 511. Plate portion 668 and handle shell 511 are sized and shaped so that the plate portion is disposed within handle cavity 534.

Finger lever or actuation element 669 extends through a slot 679 provided at the front of handle 511 and formed by aligned cut-outs in the sides of handle side portions 531a and 531b. As shown in FIG. 24, finger lever 669 extends outwardly from the arcuate end surface of pie-shaped plate portion 668. Lever 669 extends along one side of plate portion 668 so as to be centered along a line passing through bore 673.

Slave drive element 666 has a plate portion 681 which is substantially similar to plate portion 668 and provided with inner and outer surfaces 682 and 683 and a bore 684 extending therebetween at the apex of the pie-shaped plate portion 681. Pivot pin 674 extends through bore 684 in slave drive element 666. Drive elements 666 and 667 extend parallel and in juxtaposition to each other within cavity 534 with inner surface 671 of drive element 667 abutting inner surface 682 of drive element 666. Master and slave drive elements 666 and 667 can pivot independently upwardly and downwardly about pin 674.

Interengaging means is carried by master and slave drive elements 667 and 666 for removably securing the drive elements together to permit them to pivot in unison about pin 674 (see FIGS. 24 and 33). In this regard, enlarged finger lever 669 is offset toward inner surface 671 and provided with a groove 686 which extends longitudinally along the finger lever 669. Groove 686 is closed at the outer end of the lever. An elongate slide member or slide 687 is slidably captured within groove 686 and provided with a tab 688 which extends out from the side of the lever 669 at the trailing end thereof and a post 689 which extends out from the same side of the lever at the forward end thereof. Tab 688 is sized and shaped to permit it being easily grasped by the fingers of a human hand for moving slide 687 within groove 686. Plate portion 681 is provided with an enlargement 691 which extends outwardly from outer surface 683 at one end of the arcuate outer surface of slave drive element 666. A groove 692 is provided in plate portion 681 and extends through the outer arcuate surface of the plate portion in a direction toward bore 684. Groove 692 opens onto inner surface 682 of plate portion 681 and is bordered on its other side by enlargement 691. Groove 692 serves to capture the forward end of slide 687 and thus cause slave drive elements 666 to move with master drive element 667 upon manual actuation of finger lever 669 of the master drive element. A secondary groove 693 is provided in enlargement 691 for receiving post 689 when the forward end of slide 687 is disposed within primary groove 692.

A notch 694, illustrated in FIG. 23, is provided in left handle portion 531a of handle shell 531 alongside slot 679 for permitting post 689 to travel between its position outside of handle 511, shown in phantom lines in FIG. 24, and its position inside handle cavity 534 as captured within groove 693, shown in solid lines in FIG. 24.

Means is carried by handle shell 531 and drive elements 666 and 667 for releasably locking the drive elements in a home position as shown in solid and dashed lines in FIG. 24. This locking means includes a second or additional cylindrical pin 696 made from stainless steel or any other suitable material. Elongate secondary pivot pin 696 has a right end disposed within a bore 697 extending into the inside of right side portion 531b of handle shell 531 (see FIG. 32). A boss or sleeve 698 extends from the inside of left side portion 531a of handle shell 531 and is provided with a bore 699 transversely aligned with bore 697 for receiving the left end of pivot pin 696. Pin 696 extends through respective arcuate slots 703 provided in respective plate portions 668 and 681. The slots 703 are sized and shaped so as to permit the plate portions to pivot downwardly from a home position shown in FIG. 24 to various other positions shown in FIGS. 33–35 relative to handle shell 531. Plate portions 668 and 681 are further provided with respective flexible extensions or locking fingers 706 which are formed integral with the plate portions and serve to form respective capture recesses 708 for receiving pin 696 with a snap fit when the plate portions are moved to their respective home positions.

Left and right actuation assemblies 662 and 663 each further include a second drive element in the form of insulation drive 716 and a third drive element in the form of needle electrode drive 717 (see FIGS. 24 and 32–35). Each insulation drive 716 is made from polycarbonate or any other suitable material and has a first or left planar surface 718 and a second or right planar surface 719. Each insulation drive 716 is generally pie-shaped and has an outer arcuate end surface 722. A bore 723 extends through surfaces 718 and 719 adjacent the apex of each insulation drive 716. Bore 723 is sized and shaped to receive second pin 696 and permit the insulation drive to pivot about pin 696. A generally semicircular cutout extends through the bottom side of each insulation drive 716 adjacent end surface 722 and serves to engage and extend partially around pivot pin 674 for limiting the downward movement of the insulation drive 716 when it reaches its home position shown in FIG. 24.

Means is carried by each insulating sleeve 641 and insulation drive 716 for coupling the insulating sleeve 641 to the insulating drive 716 so that the insulating sleeve moves distally and proximally within the respective guide cannula 507 or 508 as the insulation drive 716 pivots upwardly and downwardly about secondary pivot pin 696. Each insulation drive 716 is provided with a block 727 formed integral therewith and extending outwardly from the end of arcuate surface 722 opposite the end adjacent cutout 724 (see FIGS. 24 and 32). Block 727 has a right surface 728 in the same plane as right surface 719 of the insulation drive 716 and an opposite left surface 729 which is spaced outwardly from and parallel with left surface 718 of the insulation drive 716. A first or left recess 731 and a second or right recess 732 are provided in first and second block surfaces 729 and 728. Elongate recesses 731 and 732 are generally identical in size and shape. The recesses 731 and 732 extend in directions generally parallel to arcuate surface 722 and are respectively provided with enlarged central portions 731a and 731b. A transversely aligned cylindrical enlargement in the form of terminal cylinder 733 is provided at the proximal end of each control tube 646 and is sized and shaped to snugly snap within the enlarged central portion of the respective recess 731 or 732. The proximal end of the control tube 646 can be further secured within recess 731 or 732 by any suitable means such as a glue (not shown). Insulation drive 716 further includes a tubular alignment sleeve 734 which circumscribes bore 723 and extends outwardly from left surface 718 around secondary pivot pin 696.

Needle electrode drives 717 are sized and shaped similar to insulation drives 716 and are each made from polycarbonate or any other suitable material. Each electrode drive 717 has a first or left planar surface 74, a second or right planar surface 742 and an arcuate end surface 743 (see FIGS. 24 and 32–35). A bore 744 extends through surfaces 741 and 742 adjacent the apex of each electrode drive 717 for receiving the alignment sleeve 734 of an insulation drive 716 to thus permit the electrode drive to pivot about secondary pivot pin 696. The cooperative engagement of bore 744 and sleeve 734 facilitates alignment of the drives 716 and 717 during their pivoting around pin 696. A cutout 746 similar to cutout 724 is provided along the bottom side of each electrode drive 717 adjacent end surface 743 and cooperatively engages pin 674 for limiting the downward travel of the electrode drive 717 within handle cavity 534.

A block 747 substantially similar to block 727 extends outwardly from the bottom of end surface 743 of each needle electrode drive 717 for securing the proximal extremity 633a of a needle electrode 633 to the drive 717 (see FIGS. 24 and 32). Block 747 is generally centered with respect to surfaces 741 and 742 and, in this regard, has left and right opposite planar surfaces 751 and 752 which are respectively spaced from surfaces 741 and 742 approximately equal distances. Left and right elongate recesses 753 and 754 are respectively provided in first and second block surfaces 751 and 752. Recesses 753 and 754 are substantially similar to recesses 731 and 732 described above and are formed with respective enlarged central portions 753a and 754a. A tubular enlargement or terminal annulus 757 made from stainless steel or any other suitable material is crimped or otherwise suitably secured to the proximal end of each needle electrode 633. Each annulus 757 is sized and shaped to snugly snap within either recess 753 or 754 and, together with block 747, is included within means for securing the proximal extremity 633a of the needle electrode to electrode drive 717.

The insulation and needle electrode drives 716 and 717 of each of left and right actuation assemblies 662 and 663 are disposed side-by-side in juxtaposition to the related drive element 666 or 667. When viewing actuation assemblies 662 and 633 from the rear, as in FIG. 32, the needle electrode drive 717 of each of actuation assemblies 662 and 663 is disposed to the left of the respective insulation drive 716 so that the right surface 742 of the electrode drive engages the left surface 718 of the insulation drive. Left actuation assembly 662 is spaced from the inside of handle left side portion 531a by sleeve 698 which extends toward assembly 662 and engages left surface 741 of the electrode drive 717. This spacing accommodates drive blocks 727 and 747 which extend to the left of the needle electrode drive 717 for left actuation assembly 662 and engage the inside of handle shell 531. Right surfaces 719 and 728 of the insulation drive 716 for right actuation assembly 663 engage the inside surface of handle right side portion 531b.

In left actuation assembly 662, terminal cylinder 733 is secured within right recess 732 of insulation drive block 727 and electrode annulus 757 is disposed in right recess 754 of needle electrode drive block 747 (see FIG. 32). Conversely, in right actuation assembly 663, terminal cylinder 733 is disposed in the left recess 731 of insulation drive block 727 and electrode annulus 757 is disposed in left recess 753 of needle electrode drive block 747. In this assembled condition, the insulation drive blocks 727 of assemblies 662 and 663 are disposed forward of the needle electrode drive blocks 747 so that the needle electrodes 633 extend proximally through insulation drive blocks 727 before being attached to electrode drive blocks 747. Insulation and electrode drives 716 and 717 are disposed relative to each other and to guide cannulas 507 and 508 so that the right recesses 732 and 754 of left actuation assembly 662 and the left recesses 731 and 753 of right actuation assembly 663 move through respective parallel planes generally containing the central axis of the respective guide cannula 507 or 508 as the drives 716 and 717 pivot about pin 696.

Interengaging or pin and slot means is carried by the insulation and needle electrode drives 716 and 717 and the drive element 666 or 667 in each of left and right actuation assemblies 662 and 663 for causing insulation drive 716 and/or needle electrode drive 717 to pivot about secondary pivot pin 696 as the drive element 666 or 667 is pivoted about primary pivot pin 674. More specifically and as identified in FIGS. 32–33, pin or reverse cam follower means is provided in the form of right drive pin assembly 761 extending generally perpendicularly from outer surface 672 of master drive element 667 and a similar left drive pin assembly 762 extending generally perpendicularly from outer surface 683 of slave drive element 666. Right drive pin assembly 762 is comprised of a cylindrical pin or post 763 formed integral with plate portion 668 and extending perpendicularly from outer surface 672 of the plate portion 668 (see FIG. 32). Left drive pin assembly 762 is similarly constructed with a cylindrical pin or post 764 formed integral with plate portion 681 and extending perpendicularly from outer surface 683 of the plate portion 681. A thin walled sleeve 767 made from any suitable material such as stainless steel is rotatably carried by each of posts 763 and 764.

The slot means is provided in insulation and needle electrode drive elements 716 and 717. In this regard, each insulation drive 716 is provided with an identical compound slot 768 extending through surfaces 718 and 719 for slidably receiving one of drive pin assemblies 761 or 762. As shown generally in FIG. 24 and specifically in FIG. 34, closed ended slot 768 has a generally linear first portion 768a corresponding to full sleeve deployment which commences adjacent block 727 and extends generally to cutout 724, a slightly arcuate second portion 768b corresponding to partial sleeve retraction which extends away from the cutout 724 at an angle of approximately 70° relative to first portion 768a and an arcuate third portion 768c which corresponds to sleeve dwell time during any partial needle retraction and extends toward bore 723 at an angle of approximately 100° relative to second portion 768b to a terminus generally adjacent sleeve 734. Each needle electrode drive 717 is provided with an identical compound slot 769 extending through surfaces 741 and 742 for slidably engaging one of drive pin assemblies 761 or 762. As shown generally in FIG. 24 and specifically in FIG. 34, slot portion 769a corresponds to full needle deployment and is generally identical to sleeve slot portion 768a. As such, slot portion 769a commences adjacent the end of arcuate surface 743 opposite block 747 and extends toward cutout 746. Slot second portion 769b corresponds to needle dwell time as the sleeve is partially retracted and extends in a direction away from arcuate surface 743 at an angle of approximately 90° relative to first portion 769a before curving slightly toward bore 744. Slot third portion 769c corresponds to partial needle retraction and extends in a direction away from cutout 746 at an angle of approximately 160° relative to slot second portion 769b before curving slightly toward bore 744.

Master drive element 667 of right actuation assembly 663 is movable about primary pivot pin 674 in its deployment stroke between a first or home position illustrated in FIG. 24 and a lower or full deployment position illustrated in FIG. 35. Finger lever 669 moves or slides through slot 679 between these positions. If dual needle electrode deployment is desired, slave drive element 666 can be coupled to master drive element 667 by means of slide 687 so that the slave drive element 666 can move with the master drive element 667 between these upper and lower positions. Insulation and electrode drives 716 and 717 of each actuation assembly 662 and 663 are pivotable either individually or together about secondary pivot pin 696 between a lower or home position shown in FIG. 24 and an upper position shown in FIG. 33.

Slots 768 and 769 are sized, shaped and positioned relative to drive pin assemblies 761 and 762 so that the relative movement between drive elements 666 and 667 and insulation and needle electrode drives 716 and 717 causes the needle electrodes 633 and insulating sleeves 641 coupled thereto to extend from and retract within left and right guide cannulas 507 and 508 in a predetermined manner. These movements of needle electrodes 633 and insulating sleeves 641 with respect to drive elements 666 and 667 will be discussed for simplicity with respect to right actuation assembly 663 only. Right needle electrode 633 and insulating sleeve 641 are sized so that when master drive element 667 is in its home position shown in FIG. 24, the electrode 633 and sleeve 641 are fully retracted within right guide cannula 508. Drive pin assembly 761 is disposed at the beginning of slot first portions 768a and 769a when master drive element 667 and insulation and needle electrode drives 716 and 717 are in these positions.

The pivoting of master drive element 667 in a counterclockwise direction about primary pivot pin 674 when handle 511 is viewed from the left as shown in FIG. 33 causes the drive element 667 to move downwardly to its second position or first intermediate position. This pivoting and movement causes drive pin assembly 761 to urge insulation and electrode drives 716 and 717 upwardly in a counterclockwise direction about secondary pivot pin 696 as the drive pin assembly 761 moves downwardly through slot first portion 768a of the insulation drive 716 and slot first portion 769a of the electrode drive 717. Sleeve 767 rotatably carried by post 763 serves as a rolling surface which facilitates movement of the drive pin assembly 761 through slot 768. The upward pivoting of insulation and electrode drives 716 and 717 causes distal extremity 633b of the needle electrode 633 and distal extremity 641b of the insulation sleeve 641 to extend in unison from the end of right guide cannula 508 a distance ranging from 20 to 30 millimeters and preferably approximately 22 millimeters.

When master drive element 667 is pivoted further downwardly about pin 674 in a counterclockwise direction to its third position or second intermediate position as shown in FIG. 34, the configuration of slot second portion 796b in electrode drive 717 permits the drive pin assembly 761 to slide therethrough without pivoting the electrode drive 717 about secondary pivot pin 696. In contrast, slot second portion 768b in insulation drive 716 is configured so that master drive element 667 causes insulation drive 716 to pivot downwardly about pin 696 in a clockwise direction to an intermediate position in which block 727 carried thereby is in close proximity to block 747 of electrode drive 717 as drive pin assembly 761 travels through the slot second portion 768b. This clockwise pivoting of insulation drive 716 causes the insulating sleeve 641 coupled thereto to retract relative to needle electrode 633 and guide cannula 508 to a partially extended position in which the insulating sleeve 641 extends beyond the end of the guide cannula 508 a distance of approximately 6 millimeters.

Further downward or counterclockwise rotation of master drive element 667 about primary pivot pin 674 to the lower position shown in FIG. 35 causes drive pin assembly 761 to move through third slot portions 768c and 769c. Slot third portion 768c of insulation drive 716 is configured so that the movement of master drive element 667 from its third position to its lower position does not cause insulation drive 716 to pivot upwardly or downwardly about secondary pivot pin 696. Thus, the insulating sleeve 641 remains relatively fixed with respect to right guide cannula 508 during this movement of master drive element 667. On the other hand, slot third portion 769c in needle electrode drive 717 is shaped so that this movement of the master drive element 667 causes needle electrode drive 717 to pivot about pin 696 downwardly in a clockwise direction relative to insulation drive 716 and thus cause the needle electrode 633 to partially retract within its coaxially mounted insulating sleeve 641.

As can be seen, left and right drive pin assemblies 761 and 762 serve as first cam elements or cam followers and plate portions 668 and 681 serve as second and third cam elements. In this manner, drive pin assemblies 761 and 762 comprise the cam assembly of transurethral needle ablation device 506 and serve as reverse cam followers which cooperatively engage plate portions 668 and 681 to drive the same. The cam assembly of the present invention is a closed track cam and, as such, does not require a spring to keep the cam followers in contact with the cam. This cam assembly has the advantage of positive drive throughout the deployment and resetting strokes of left and right actuation assemblies 662 and 663. Although the cam and cam follower means are described to include drive pin assemblies 761 and 762 and plate portions 668 and 681, it should be appreciated that other cam and cam follower means can be provided and be within the scope of the present invention.

Adjustable stop means is carried by handle 511 for selectively predetermining the lower position of master drive element 667 in handle 511 and thus the distance which needle electrodes 633 fully deploy from guide cannulas 507 and 508. The stop means includes a stop element or stop block 776 provided with left and right cylindrical pins 777 and 778 formed integral therewith and extending in transversely aligned positions from opposite sides of the stop block 776 (see FIGS. 33 and 34). Pins 777 and 778 are respectively disposed within transversely-aligned bores 781 provided in left and right side portions 531a and 531b of handle shell 531. Stop block 776 is carried by pins 777 and 778 for pivotal movement with respect to handle 511 and has a cross-section, as illustrated in FIG. 24, which is pentagonal in shape.

At least four of the five surfaces forming the pentagonal shape of stop block 776 are generally planar and spaced from the center of bore 781 respective predetermined distances. The closer one of these surfaces is to the center of bore 781 the farther drive element 667 is permitted to pivot downwardly if at all from its third position and the farther drive pin assembly 761 extends through third slot portion 768c. As discussed above, the distance which needle electrode 633 partially retracts within guide cannula 508 corresponds directly to the distance which drive pin assembly 761 travels through third slot portion 768c and the related clockwise pivoting of needle electrode drive 717. First surface 782 is spaced from and aligned relative to the center of bore 781 so that the needle electrode 633 extends from the distal end of guide cannula 508 a distance of approximately 14 millimeters. Second and third surfaces 783 and 786 are respectively distanced from the center of bore 781 and aligned so that the needle electrode 633 extends from guide cannula 508 respective distances of 17 and 20 millimeters. Fourth surface 787 corresponds to a needle electrode 633 extension of 22 millimeters and thus precludes further pivoting of drive element 667 from its third position shown in FIG. 34 and related partial retraction of the needle electrode when the full extension distance of the needle electrode 633 in the third position is approximately 22 millimeters. Master drive element 667 has a bottom side surface 788 which is generally planar for engaging the planar surfaces 782, 783, 786 and 787 of stop block 776. In FIG. 35, it can be seen that bottom surface 788 is engaging second surface 783 of the stop block 776 so that needle electrode 633 extends approximately 17 millimeters beyond guide cannula 508.

Knob or pointing means in the form of knob 791 is provided for manually rotating stop block 776 relative to handle 511 (see FIGS. 23 and 24). Knob 791 has a tapered end 793 which thus serves as a pointer. The numbers 14, 17, 20 and 22 are set forth on the outside of handle shell side portion 531a in spaced positions around pointer knob 791 so that the tapered end 793 of pointer knob 791 aligns with the appropriate number to indicate which surface 782, 783, 786 or 787 is engaging master drive element 667 inside handle shell 531.

An electrical pin connector 801 is provided at the bottom of handle 511 for permitting electrical contact with needle electrodes 633 and first and second thermocouples 656 and 657. Lead or wire means in the form of wires 803 are provided and have one end electrically connected to needle electrodes 633 at terminal annuluses 757 and the other end joined to connector 801. First and second thermocouple leads 658 and 659, not shown for simplicity in FIGS. 24 and 33–35, extend from the proximal ends of insulating sleeves 641 alongside proximal extremities 633a of needle electrodes 633 and wires 803 to connector 801. The pin connector 801 is adapted for electrical connection to a cable 806 which is connected at its other end to a radio frequency generator and controller 807 substantially similar to generator and controller 367 described above.

Coupling means adapted to alternatively secure at least first and second endoscopes to the proximal end of sheath 452 is carried by the proximal extremity of sheath 452 and, more specifically, transurethral needle ablation device 506. The endoscope coupling means permits device 506 to be utilized with endoscopes 26, 381, 421 and 436 described above and includes first adapter means in the form of rear portion 537c of articulation of 537 for mounting Olympus endoscope 26 on handle 511 and sheath 452. Rear or disk portion 537c, as shown in FIGS. 24 and 36, has a generally planar rear surface 812 extending perpendicular to central longitudinal axis 454. Surface 812 is formed in part by a wall 813 which also serves as a portion of the periphery of an internal recess 816 provided below central bore 538 and opening onto the bottom of disk portion 537. A bore 817 extends through wall 813 in a direction generally parallel to axis 434 into recess 816. Bore 815 is sized to slidably receive coupling extension 32 of endoscope 26. A pair of generally parallel spaced-apart elongate retention elements 818 extend generally downwardly from the center of disk portion 537c into internal recess 816. The retention elements 818 are centered so that endoscope coupling extension 32 is disposed therebetween when extending through bore 817. An annular grove 821 provided on coupling extension 32 is generally centered between the retention elements 818 and permits the coupling extension to fit between retention elements 818 with a snap fit for rotatably and longitudinally locking endoscope 26 to handle 511. In this manner, retention elements 818 are included within the cooperative means of disk portion 537c for mating with coupling extension 32 of endoscope 26 to rotatably and longitudinally lock the endoscope 26 to articulation hub 537.

Sheath 452 and disk portion 537c are longitudinally sized so that when fitting 31 of endoscope 26 is in engagement with rear surface 812 of articulation hub disk portion 537c, viewing face 28 of the endoscope is generally disposed at distal opening 458 of sheath 452 as illustrated in FIG. 26. Optical element 27 of endoscope 26 extends through central bore 538 of articulation hub 537, through opening 478 in hub 472 and into upper portion 457a of sheath central passageway 457. As such, optical element 27 extends through sheath 452 adjacent to and more specifically above left and right guide cannulas 507 and 508.

The endoscope coupling means of transurethral needle ablation device 506 further includes second adapter means in the form of removable first adapter 831 for adapting needle ablation assembly 451 for use with Circon ACMI endoscope 381 described above. As illustrated in FIGS. 17, 37 and 38, endoscope 381 includes a cylindrical coupling extension 388 provided with an annular groove 832 extending circumferentially thereabout. First adapter 831 is formed from a cylindrical body 833 made from any suitable material such as polycarbonate which is generally circular in cross-section and has proximal and distal extremities 833a and 833b (see FIGS. 37–38). Means is carried by adapter distal extremity 833b and disk portion 537c of articulation hub 537 for attaching adapter 831 to device 506. In this regard, disk portion 537c is provided with a pair of transversely aligned posts 836 formed integral therewith and extending radially outwardly from opposite sides thereof. Cylindrical body 833 is provided with a recess 837 formed by a cylindrical wall 838 for receiving disk portion 537c. Wall 838 is provided with a pair of diametrically aligned L-shaped slots 841 which each form a circumferentially-extending flexible finger 842. A detent 843 is provided on the inside of each flexible finger 842 and opens into slot 841.

Adapter 831 is mounted to disk portion 537c by sliding body 833 longitudinally onto the disk portion 537c when first and second posts 836 are in angular registration with the longitudinal portion of respective first and second slots 841. Adapter 831 is then rotated in a clockwise direction about longitudinal axis 454 so that posts 836 travel through the circumferential portion of slots 841. Fingers 842 are shaped so as to flex and permit posts 836 to travel circumferentially through the slots 841 until the posts 836 engage detents 843 with a snap fit. Cylindrical body 833 is provided with a plurality of longitudinally-extending recesses or indentations 846 spaced circumferentially thereabout for facilitating the gripping and rotation of adapter 831 by the fingers of a human hand.

An elongate extension 847 protrudes longitudinally from the outside of body distal extremity 833b for properly registering adapter 831 on articulation hub disk portion 537c. More specifically, extension 847 cooperates with handle 511 to permit adapter 831 to be mounted on disk portion 537c only if the adapter 831 is angularly positioned so that extension 847 extends along the top of the adapter and the handle. If adapter 831 is aligned otherwise with respect to handle 511, for example extension 847 is extending along the bottom of the adapter, extension 847 engages the rear of handle shell 531 below disk portion 537c and thus precludes posts 836 from entering the longitudinal portion of slots 841.

Proximal extremity 833a of cylindrical body 833 includes cooperative means for mating with coupling extension 388 of endoscope 381 so as to longitudinally and rotatably secure endoscope 381 to adapter 831 and device 506. Adapter 833 is provided with a proximal planar surface 851 which extends generally perpendicular to the longitudinal axis of adapter body 833. A bore 852 extends through surface 851 along this longitudinal axis and is aligned with central bore 538 of articulation hub 537 for slidably receiving optical element 382 of endoscope 381. Body proximal extremity 833a is provided with a recess 853 which extends through the bottom thereof and through proximal surface 851. A pair of spaced-apart clamping members 856 are formed integral with body 833 and depend parallel to each other within recess 853. Clamping members 856 are spaced apart a sufficient distance so as to permit coupling extension 388 to extend therebetween when endoscope 381 is coupled to adapter 831 with light post 387 in a downwardly depending position. clamping members have vertically-extending opposed ribs 857 on the inside surfaces thereof for seating in annular groove 832 of coupling extension 388. In this manner, coupling extension 388 engages clamping members 356 with a snap fit to longitudinally and rotatably lock endoscope 381 to adapter 831. The clamping members 356 are thus included within the means of first adapter 831 for rotatably and longitudinally locking endoscope 381 thereto.

Cylindrical body 833 is longitudinally sized so that the viewing face at the distal end of endoscope optical element 382 is disposed adjacent sheath distal opening 458 in a manner similar to the position of viewing face 28 of endoscope 26 shown in FIG. 26.

Third adapter means in the form of removable second adapter 866 is included within the endoscope coupling means of transurethral needle ablation device 506 to adapt needle ablation assembly 451 for use with the Wolf endoscope 421 described above. As shown in FIGS. 21 and 40, endoscope 421 includes a plate-like coupling extension 426 which is generally rectangular in shape. Coupling extension 826 has opposite ears 867 that extend beyond the outer circular periphery 868 of the portion of endoscope fitting 423 which adjoins the proximal surface of coupling extension 426. Ears 867 each have rounded outer ends 869.

Second adapter 866 is formed from a cylindrical body 872 made from polycarbonate or any other suitable material which is circular in cross-section and has proximal and distal extremities 872a and 872b (see FIGS. 39–41). Body 872 has an outer cylindrical wall 873 and is provided with an internal cavity 874 which is cylindrical in shape. Distal extremity 872b is sized, shaped and configured substantially similar to distal extremity 833b of cylindrical body 833 and like reference numerals have been used in FIG. 39 to describe like components of cylindrical bodies 833 and 872. Slots 841, fingers 842 and detents 843 permit adapter 866 to mount on disk portion 537c of articulation hub 537 in the same manner described above with respect to first adapter 831.

Cylindrical body 872 is provided with a proximal wall 876 which is adapted to couple with fitting 423 of endoscope 421. Proximal wall 876 is provided with an opening 877, shown in FIG. 40, which is generally rectangular in shape from side to side and further configured to permit coupling extension 426 of endoscope 421 to pass therethrough when endoscope 421 is rotated from its upright position by an angle of approximately 90° relative to its longitudinal axis.

Means is carried by adapter 866 for providing a friction fit between the proximal surface of endoscope ears 867 and the inside of proximal wall 876 once coupling extension 426 has passed through opening 827. This means includes planar spring means in the form of spring plate 881 which is generally annular in shape and made from spring steel or any other suitable material. Spring plate 881 has a peripheral portion 882 for defining a central opening 883. Cylindrical body 872 includes first and second diametrically opposed channels 886 formed inside cylindrical wall 883 adjacent proximal wall 876 and defined by spaced-apart side walls 887. Channels 886 serve to receive first and second radially-extending extensions or tangs 891 formed on the outside of peripheral portion 882 (see FIG. 40). Each tang 891, as shown in FIG. 42, has an outer portion 891a which inclines outwardly from the plane of spring plate 881.

Spring plate 881 is mounted inside second adapter 866 by disposing the spring plate adjacent proximal wall 876 with tang outer portions 891a inclined away from the proximal wall 876. Spring plate 881 is aligned so that tangs 891 are in registration with channels 886 and is then pressed against proximal wall 876. Tangs 891 are longitudinally sized so as to engage the inside of cylindrical wall 873 and inhibit the spring plate 881 from pulling away from proximal wall 876. Central opening 883 in spring plate 881 has a size and shape as least as large as opening 877 in proximal wall 876 so as to permit coupling extension 426 of endoscope 421 to pass therethrough.

Spring plate 881 is engaged when endoscope 421 is rotated in a clockwise direction approximately 90° about its longitudinal axis to its upright position following insertion of coupling extension 426 through opening 877 of cylindrical body 872 and opening 883 of spring plate 881. Peripheral portion 882 has first and second flexible portions in the form of spring fingers 896 formed by first and second slots 897 extending through the peripheral portion 882 and opening into central opening 883 of the spring plate 881. Spring fingers 896 each have an arcuate shape when viewed in plan, as in FIG. 40, and extend around a portion of the inside of peripheral portion 882 in spaced-apart diametrically opposed positions. Each spring finger 896 has a central portion 896a which bows outwardly away from proximal wall 876 as illustrated in the side elevational view of spring 881 in FIG. 41 and the cross-sectional view of the spring plate in FIG. 43. Spring fingers 896 are sized and shaped so that the proximal surfaces of endoscope ears 867 ride up onto central portions 896a when endoscope 421 is rotated approximately 90° relative to spring plate 881. The frictional engagement between spring fingers 896 and ears 867 serves to rotatably lock endoscope 421 with respect to second adapter 866 while the engagement of spring fingers 896 and proximal wall 876 with ears 867 serves to longitudinally lock endoscope 421 to adapter 866. Spring plate 881 and proximal wall 876 are thus included within the means of adapter 866 for locking endoscope 421 to the adapter.

First and second protuberances in the form of stops 898 extend from the inside of proximal wall 876 for limiting the locking rotation of endoscope 421 relative to adapter 866. As illustrated in FIG. 40, blocks 898 extend through respective slots 897 and engage the sides of ears 867 upon rotation of endoscope 421 to its upright position with light post 427 extending downwardly. Second adapter 866 is longitudinally sized so that the viewing face of endoscope optical element 422 is disposed at distal opening 458 of sheath 452 in the same manner as illustrated in FIG. 26 with respect to viewing face 28 of optical element 27 when the proximal extremity of endoscope 421 is mounted to the adapter 866.

Transurethral needle ablation device 506 is adapted for use with fourth adapter means in the form of removable third adapter 901 which permits needle ablation assembly 451 to be used with the Storz endoscope 436 described above. As shown in FIGS. 22, 44 and 45, endoscope 436 has a coupling extension 438 provided with first and second ears 902 which extend beyond the cylindrical outer periphery 903 of endoscope fitting 904 disposed proximal of ears 902. Ears 902 extend in diametrically opposite directions in a plane disposed generally perpendicular to the longitudinal axis of endoscope 436. An optical element 906 carrying rod lens 437 extends distally from fitting 904.

Third adapter 901 is substantially similar to second adapter 866 and is formed from a body 907 provided with an outer cylindrical wall 908 defining an internal cylindrical cavity 909. Body 907 has a distal extremity (not shown) which is substantially identical to distal extremity 872b of second adapter body 872 for permitting adapter 901 to mount on disk portion 537c of articulation hub 537 in the same manner that second adapter 866 mounts to the disk portion 537c. Cylindrical body 907 has a proximal extremity 907a which includes a proximal wall 911 extending at a substantially right angle to the longitudinal axis of cylindrical body 907. An opening 912 extends through proximal wall 911 and is sized and shaped for permitting coupling extension 438 and ears 902 thereof to pass therethrough after endoscope 436 is rotated about its longitudinal axis through an angle of approximately 90° relative to its generally upright position.

Cylindrical body 907 has diametrically opposed channels 913 substantially similar to channels 886 described above and defined by side walls 914 substantially similar to side walls 887. Channels 913 are formed on the inside of cylindrical wall 908 adjacent proximal wall 911 for receiving tangs 891 of spring plate 881 as shown in FIGS. 44 and 45. Central opening 883 in spring plate 881 is sized and shaped to permit coupling extension 426 to pass therethrough. Spring fingers 896 bow outwardly from proximal wall 911 in the same manner as discussed above with respect to second adapter 866 so as to frictionally engage the proximal surfaces of ears 902 when endoscope 436 is rotated about its longitudinal axis in a clockwise direction through an angle of approximately 90° relative to third adapter 901. In this manner, spring plate 881 serves to rotatably and frictionally lock endoscope 436 to device 506 and spring plate 881 and proximal wall 911 are included within the means of third adapter 901 for locking endoscope 436 to the adapter. First and second diametrically opposed protuberances in the form of stops 916 extend from the inside of proximal wall 911 for limiting the rotatable travel of ears 902 within third adapter 901. Stops 916 extend through slots 897 in spring plate 881 to engage the side of ears 902 as shown in FIG. 44.

Third adapter 902 is longitudinally sized so that when endoscope fitting 904 is in locked engagement with adapter proximal wall 911, optical element 906 extends through sheath passageway 457 so that the distal viewing face of optical element 906 is disposed at sheath distal opening 458 in a manner similar to that illustrated in FIG. 26 with respect to viewing face 28 of endoscope 26.

In operation and use, transurethral needle ablation device 506 can serve as an adjustable electrosurgical cartridge for performing an electrosurgical procedure on tissue at a treatment site within a human body in the same manner as described above with respect to device or handle 23. Alternatively, device 506 can be utilized for performing a procedure of the type described in detail in copending U.S. patent application Ser. No. 08/191,258 filed Feb. 2, 1994 on a human male patient. The procedure can briefly be described as follows.

The anatomy of interest in the male patient to undergo the procedure consists of a bladder which is provided with a base or bladder neck which empties into a urethra extending along a longitudinal axis. The urethra can be characterized as being comprised of two portions: a prostatic portion and a penile portion. The prostatic portion is surrounded by a prostate or prostate gland which is a glandular and fibromuscular organ lying immediately below the bladder. The penile portion of the urethra extends through the length of a penis. The urethra is provided with a urethral wall which extends through the length of the penis and through the prostate into the bladder. The prostate can be characterized as being comprised of five lobes: interior, posterior, median, right lateral and left lateral. The prostate is also provided with a verumontanum. The size of the prostate to be treated is determined by the operating physician in a conventional manner such as via rectal ultrasound.

Once the patient has been prepared, a conventional indifferent or grounding electrode is placed on the patient's backside so that it is adherent thereto and makes good electrical contact with the skin of the patient. The electrode is connected by an electrical cable (not shown) into control console and radio frequency generator 807. A conventional foot operated switch (not shown) can be connected by a cable into the console 807 for controlling the application of radio frequency power.

Needle ablation assembly 451 is prepared by mounting transurethral needle ablation device 506 on sheath 452. In this regard, left and right guide cannulas 507 and 508 are introduced into opening 478 of hub 472 and then inserted into central passageway 457 of the sheath 452 with master drive element 667 in its home or upper position so that left and right stylets 631 and 632 are fully retracted within the guide cannulas 507 and 508. Left and guide cannulas 507 and 508 are elevationally aligned relative to the articulation hub 537 so that they extend along lower portion 457b of sheath passageway 457. As distal extremities 517 of the guide cannulas 507 and 508 approach distal opening 458 of sheath 452, front portion 537a and transversely aligned ears 561 and 562 of articulation hub 537 are inserted into hub internal cavity 477 so that ears 561 and 562 are disposed in respective recesses 563 and 564 distal of lip portions 486 of optic lock collar 481. Manual rotation of the optic lock collar 481 by means of radius bar 492 in a clockwise direction when viewing collar 481 from the rear causes lip portions 486 to likewise rotate and engage the backside of ears 561 and 562 so as to secure device 506 to sheath 452.

The operating physician selects one of the four conventional endoscopes 26, 381, 421 or 436 and mounts the appropriate adapters 831, 866 or 901, if necessary, to posts 836 on articulation hub disk portion 537c in the manner discussed above. The optical element of the endoscope is inserted through central bore 538 of the articular hub into upper portion 457a of sheath central passageway 457 as discussed above. The distal viewing face of the endoscope is disposed at sheath distal opening 458 when the endoscope is longitudinally locked either directly or indirectly to articulation hub 537.

A suitable light source is connected to the light post of the endoscope and radio frequency generator and controller 807 is connected to device 506 by cable 806. A source of a suitable flushing fluid such as a saline solution is coupled to first and second stopcocks 496 and 497 to permit introduction and/or withdrawal of a saline solution or other fluid through sheath passageway 457 during the procedure.

Catheter sheath 452 is adapted for insertion into a natural body opening such as the urethra. Prior to insertion, the operating physician introduces an anesthetic such as Lidocaine into the urethra by means of a needleless syringe and coats sheath 452 with an anesthetic. The operating physician then positions needle ablation assembly 451 with handle 511 extending upwardly and grasps handle 511 with one hand to introduce sheath distal extremity 453b into the urethra. The front configuration of tube extension 462 facilitates insertion of sheath 452 into the urethra and its passage therethrough. In this regard, the drooping bulbous tip 464 and the rear inclination of front surfaces 466 inhibit the formation of trauma as extension 462 passes along the urethral wall. The narrowing and tapering of extension 462 at front wall portions 463a facilitates opening of the urethra to permit passage of sheath 452. The elevated front wall portions 463a of tube extension 462 shield the urethral wall from snagging on distal extremities 517 of left and right guide cannulas 507 and 508 should flexible portions 517a of guide tubes 513 have any upward permanent or residual bend while in their straightened-most positions. Sheath distal extremity 453b is advanced through the urethra until it is in the vicinity of the prostate. A steady flow of flushing fluid introduced into the urethra via passageway 457 facilitates viewing the urethral wall with the endoscope so that the operating physician can ascertain when the distal end of sheath 452 is in desired registration with the prostate. Sheath 452 has a length which is sufficient to permit the distal end thereof to be in the vicinity of the prostate when the proximal end thereof is outside of the urethra.

Transurethral needle ablation device 506 can now be utilized to perform a needle ablation procedure on the prostate in the manner set forth in U.S. patent application Ser. No. 08/191,258 filed Feb. 2, 1994. If, for example, treatment is desired in the left and/or right lateral lobes of the prostate, the operating physician rotates assembly 451 approximately 90° about axis 454. Flexible portions 517a of guide cannulas 507 and 508 are then bent to the desired angle between 0 and 90° relative to longitudinal axis 454 by proximal movement of lever tab 408 relative to handle shell 531 so that ports 519 are pointed toward the urethral wall. When treating a lateral lobe, for example, lever tab 609 is pulled to its full proximal or rearward position shown in phantom lines in FIG. 24 so that flexible portions 517a extend through an angle of approximately 90°. Ports 519 thus face the lateral lobe of the prostate being treated. Alternatively if for example treatment of the median lobe is desired, lever tab 609 is pivoted only slightly about pin 611 so that the flexible portions 517a of guide cannulas 507 and 508 bend only through an angle of approximately 10°.

Cooperatively interengaging detents 622 and spring loaded pin 611 facilitate the retention of flexible portions 517a of left and right guide cannulas 507 and 508 at certain predetermined angles. L-shaped slots 526 provided in flexible portions 517a of guide tubes 513 permit relatively smooth bending of the guide tubes. The L-shaped slots 526 permit the portions of guide tubes 513 between the slots to interlock at the slots as shown in FIG. 26 and thus provide rigidity to the bent guide cannulas 507 and 508.

Either right stylet 632 individually or left and right stylets 631 and 632 together can be extended from guide cannulas 507 and 508 during the needle ablation procedure. If it is desired that only the right stylet be deployed, selection slide 687 is moved to its outward position so that the forward end thereof is disengaged from capture groove 692 in slave drive element 666 as shown in phantom lines in FIG. 24. As discussed above, notch 694 allows post 689 to move in and out of handle cavity 534 when drive elements 666 and 667 are in their respective home positions shown in FIG. 24. On the other hand, if both stylets 631 and 632 are to be introduced into the tissue of the prostate, slide 687 is moved to its forward position so that the front end thereof is disposed within capture groove 692 and post 689 is received within groove 693. As so interlocked, master and slave drive elements 667 and 666 move together about pin 674. The engagement of post 689 with the inside wall of handle shell 531 adjacent slot 679 precludes the withdrawal of slide 687 from capture grooves 692 and 693 while drive elements 666 and 667 are in other than their home positions, such as their operational positions illustrated in FIGS. 33–35. In the following discussion, let it be assumed that the operating physician wishes to deploy both left and right stylets 631 and 632.

Prior to deployment of stylets 631 and 632, the operating physician rotatably adjusts pointer knob 791 so that the final extension position of needle electrodes 633 corresponds to the size of the prostate being treated. As discussed above, transurethral needle ablation device 506 permits the distal tip of the needle electrodes to extend approximately 14, 17, 20 or 22 millimeters beyond the distal end of guide tube 513 by predetermining which of stop surfaces 782, 783, 786 or 787 will engage bottom surface 788 of master drive element 667 when element 667 is pivoted to its lowermost position within handle 511.

In positioning for stylet deployment, the operating physician wraps the fingers of one hand around handle shell 531 with one or more fingers disposed between sheath hub 472 and finger lever 669. The operating physician then pulls on finger lever 669 with one or more fingers in a continuous downward stroke to deploy left and right stylets 631 and 632 from the guide cannulas. Movement of left and right drive elements 666 and 667 from their upper or home positions to their first intermediate positions causes needle electrodes 633 and insulating sleeves 641 to fully extend from guide tubes 513 to the preferred 22 millimeter distance indicated above. During this deployment, the needle electrodes and insulating sleeves pass through the urethral wall into the target tissue of the prostate. The operating physician can view the stylets 631 and 632 being so deployed sidewise of the longitudinal axis 454 of assembly 451 through the endoscope. Viewing through the endoscope is particularly enhanced when the optical element of the endoscope is provided with a viewing face such as viewing face 28 which is disposed at an oblique angle relative to the central axis of the optical element.

Further downward or clockwise pivoting of master and slave drive elements 667 and 666 about primary pivot pin 674 causes insulating sleeves 641 to retract within guide tubes 513 relative to needle electrodes 633 so that the distal end of the insulating sleeves are distanced from the end of guide tubes 513 as indicated above. This retraction of insulating sleeves 641 serves to reduce if not eliminate any outward bowing or tenting of the urethral wall which may have occurred during penetration of the urethral wall and introduction of stylets 631 and 632 into the target volume of tissue in the prostate. The insulating sleeves 641 are sized and actuation assemblies 662 and 663 configured so that distal extremities 641b of the insulating sleeves remain extended beyond the urethral wall when so moved to their retracted positions. Where the selected final extension position of needle electrodes 633 is 22 millimeters, drive element bottom surface 788 engages fourth surface 787 at this point on the drive stroke and stop block 776 thus precludes further downward pivoting of the drive element. The third position of drive elements 666 and 667 shown in FIG. 34 is thus the lower position of the drive elements in this setting of pointer knob 791.

If pointer knob 791 is directed to either 14, 17 or 20 millimeters, the operating physician further pivots drive elements 667 and 666 in the continuous downward stroke until bottom side surface 788 of master drive element 667 and the corresponding surface of slave drive element 666 engage the predetermined surface 782, 783 or 786 of stop block 776. As discussed above, this movement of drive elements 667 and 666 from their second intermediate positions to their lower operational positions causes needle electrodes 633 to retract relative to guide tubes 513 to the predetermined distance corresponding to the engaged surface 782, 783 or 786.

Sheath tube extension 462 serves to support and retain flexible portions 517a of guide tubes 513 against the forces exerted by the urethral wall against the penetrating stylets 631 and 632. The bottom portion of tube extension 462 restricts flexible portions 517a from bending backwardly against these forces. Flared wall portions 463b preclude flexible portions 517a from bending outwardly away from each other by cradling flexible portions 517a in their bent or articulated position as shown in FIG. 26 so that the flexible portions 517a splay at an angle ranging from 30° to 50°. The narrowing of sheath extension 462 at front wall portions 463a facilitates this cradling of flexible portions 517a, particularly when the flexible portions are bent to their maximum angle of approximately 90°. In this manner, sheath 452 permits more accurate placement of electrode distal extremities 633b during the ablation procedure.

Once left and right stylets 631 and 632 have been so placed within the target prostatic tissue to be ablated, radio frequency energy is supplied by means of RF generator and controller 807 to needle electrodes 633 so as to be conducted through the tissue of the prostate to the return or indifferent electrode provided on the outside of the patient. In this manner, lesions are created in the target volume of prostatic tissue in the vicinity of the exposed portions of the needle electrodes 633. These lesions serve to shrink the size of the prostate. First thermocouples 656 carried by insulating sleeves 641 of each stylet 631 and 632 are disposed within the prostate and permit measuring of the temperature of the tissue being ablated. Second thermocouples 657 are disposed in the urethra in the vicinity of the urethral wall and permit monitoring of the temperature within the urethra during the ablation procedure. The information from second thermocouples 657 can be utilized to ensure that the urethral wall is not damaged by the ablation procedure. The endoscope permits the operating physician to view the urethral wall during the procedure.

It should be appreciated that transurethral needle ablation device 506 can be used for performing a bipolar ablation and be within the scope of the present invention. In such a procedure, radio frequency energy would be supplied through one of needle electrodes 633 for conduction through the tissue to be ablated and returned through the other needle electrode 633. Radio frequency generator and controller 807 is capable of providing both monopolar and bipolar radio frequency outputs at relatively low power of up to 50 watts.

Once lesions have been so created in the desired target volume of the prostate, the operating physician pivots finger lever 669 in a clockwise or upper direction about primary pivot pin 674 to reverse the deployment stroke of left and right actuation assemblies 662 and 663. Needle electrodes 633 and insulating sleeves 641 reverse their deployment movements in this resetting stroke of the actuation assemblies. Electrodes 633 and sleeves 641 thus extend fully. into the prostatic tissue before retracting into the guide tubes 513 of left and right guide cannulas 507 and 508. The engagement of post 689 with the inside wall of handle shell 531 adjacent slot 679 precludes the disengagement of slave drive element 666 from master drive element 667 during this needle and sleeve retraction step. Upon return of master and slave drive elements 667 and 666 to their respective home positions, respective locking fingers 706 snap around secondary pivot pin 696 to retain the drive elements in these position. Lever tab 609 is then moved to its distalmost position, shown in solid lines in FIG. 24, so that flexible portions 517a of guide tubes 513 generally straighten within sheath 452 and the distal tips of the guide cannulas retract within elongate tube extension 462 of sheath 452. In connection with such straightening, the relatively rigid push/pull ribbon 571 carried within guide tubes 513 permits compressive forces to be exerted axially on flexible portions 517a of the guide tubes 513 to straighten or extend the flexible portions 517.

In a typical procedure, further ablations are performed in other target regions or areas within the prostate. Preparatory to these further ablations, needle ablation assembly 451 is rotated within the urethra. Elevated front wall portions 463a of tube extension 462 protect the urethral wall from engaging distal extremities 517 of guide cannulas 507 and 508 during such rotation of sheath 452. Flexible portions 517a of the guide cannulas can be then bent to a desired position to properly direct stylets 631 and 632 into this additional portion or region of the prostate. Stylets 631 and 632 are redeployed by means of drive elements 667 and 666 in the same manner as discussed above and radio frequency supplied thereto to create additional lesions in the prostate.

Once the needle ablation procedure has been completed, any further medicament such as an anesthetic can be introduced through sheath passageway 657 by means of one or both stopcocks 496 and 497. The operating physician can now withdraw needle ablation assembly 451 from the urethra.

Following disassembly of needle ablation assembly 451, sheath 452 and the endoscope can be easily sterilized for reuse. As discussed above, sheath 452 permits other endoscopes to be utilized therewith in further procedures.

As can be seen, trigger assembly 661 and the pin and slot means carried by drive elements 666 and 667 and insulation and needle electrode drives 716 and 717 permit full extension and partial retraction of needle electrodes 633 and insulating sleeves 641 in a single continuous stroke of finger lever 669 in a single direction. Dedicated actuation elements for each of needle electrode deployment and insulating sleeve deployment are not provided. This continuous downward stroke of a single actuation or slide element facilitates use of device 506 because it eliminates any need for the operating physician to move fingers between multiple actuation elements during the procedure to fully deploy the needle electrodes and insulating sleeves. Repeatability and standardization of procedures is also assured because needle electrodes 633 and insulating sleeves 641 deploy in exactly the same manner with each downward stroke of finger lever 669. Only the final extension position of needle electrodes 633 varies depending upon the selected position of pointer knob 791. There is a direct correlation between the position of finger lever 669, the position of drive elements 666 and 667 and drives 716 and 717 and the position of electrodes and sleeves 633 and 641; no springs or similar automatic mechanisms having variable positions independent of the position of finger lever 669 are included in needle ablation assembly 451.

Although transurethral needle ablation device 506 provides for independent partial retraction of needle electrodes 633 and insulating sleeves 641, it should be appreciated that a device providing for simultaneous retraction of electrodes 633 and sleeves 641 could be provided and be within the scope of the present invention. In addition, although needle ablation assembly 451 and transurethral needle ablation device 506 have been described in connection with electrosurgical and transurethral needle ablation procedures, it should be appreciated that they can be used for performing other procedures in other canals in the human body defined by canal walls. As part of these other procedures, the distal extremity of assembly 451 and/or device 506 can be introduced through a natural body opening into such a canal and advanced therein for diagnosis, treatment or other purposes. Device 506 can also be utilized in performing procedures through other openings in the body such as an incision.

It should also be appreciated that needle ablation assembly 451 and transurethral needle ablation device 506 can be used with other treatment modalities such as resistive heating or microwave and be within the scope of the present invention.

In view of the foregoing, it can be seen that a new and improved electrosurgical catheter has been provided which can be adapted for use with a plurality of conventional rod lens endoscopes. The catheter includes a reusable sheath and at least one needle electrode which can be advanced sidewise of the longitudinal axis of the catheter at a selected angle ranging from 0° to 90°. A second needle electrode can be provided which can be selectively advanced or not advanced with the first needle electrode. The catheter permits a generally unobstructed view of the needle electrodes advancing toward the target region in the body and includes guide cannulas provided with slots for providing a relatively smooth bend in the guide cannulas. A substantially rigid pull/push member is provided in the guide cannulas for bending and straightening of the guide cannulas.

Insulation means can be coaxially disposed on the needle electrode and an actuation element provided for extending and partially retracting the insulation means in a single stroke of the actuation element. The actuation element can extend and partially retract the needle electrode and the insulating means in a single stroke of the actuation element. The device includes adjustable stop means for selectively stopping the actuation element at a predetermined position so as to limit any partial retraction of the needle electrode and can be utilized for performing a transurethral needle ablation procedure. In such a procedure, the needle electrode can be advanced into the tissue of the prostate and radio frequency energy supplied thereto for creating a lesion in the prostate. The insulation means is extended into the tissue of the prostate and then partially retracted prior to supplying radio frequency energy to the needle electrode. The device permits the needle electrode to be extended into the tissue of the prostate and then partially retracted prior to the supply of radio frequency energy to the needle electrode.

What is claimed is:

1. A medical device for treatment of tissue at a treatment site through a body opening comprising an elongate probe member having proximal and distal extremities and having a passageway extending from the proximal extremity to the distal extremity, a guide tube mounted in the passageway of the elongate probe member and having proximal and distal extremities and a lumen extending from the proximal extremity to the distal extremity, a needle electrode slidably mounted in the lumen of the guide tube and having proximal and distal extremities, insulation means coaxially disposed on the needle electrode, handle means adapted to be gripped by the human hand coupled to the proximal extremity of the elongate probe member, first actuator means carried by the handle means and connected to the guide tube for causing bending of the distal extremity of the guide tube at an angle with respect to the longitudinal axis whereby the lumen in the guide tube can be directed so that it faces the tissue to be treated, connector means connected to the needle electrode adapted to be coupled to an energy source for supplying energy to the needle electrode and second actuator means carried by the handle means and coupled to the needle electrode and the insulation means for advancing and retracting the needle electrode and the insulation means with respect to the guide tube and including a single actuation element movable in a single stroke from a first position in which the needle electrode and the insulation means are disposed within the guide tube to a second position in which the needle electrode and the insulation means are disposed in the tissue at the treatment site and to a third position in which the insulation means is retracted partially relative to the needle electrode.

2. A device as in claim 1 wherein the actuation element is a finger lever.

3. A device as in claim 1 wherein the second actuator means includes first, second and third plate members disposed within the handle means in juxtaposition, the first plate member connected to the actuation element and pivotable about a first axis, the second and third plate members respectively connected to the needle electrode and the insulation means and pivotable about a second axis, interengaging pin and slot means carried by the plate members for directing the movement of the second and third plate members about the second axis in response to movement of the first plate member about the first axis.

4. A device as in claim 1 wherein the second actuator means includes first, second and third plate members disposed in juxtaposition within the handle, the first plate member connected to the actuation element and pivotable about a first axis, the second and third plate members respectively connected to the needle electrode and the insulation means and pivotable about a second axis, interengaging pin and slot means carried by the plate members for directing the movement and sequence of the second and third plate members about the second axis in response to movement of the first plate member about the first axis.

5. A device as in claim 1 wherein the second actuator means includes a cam assembly having a first cam element connected to the actuation element and second and third cam elements respectively connected to the needle electrode and the insulation means for cooperatively engaging with the first cam element.

6. A device as in claim 1 further comprising a guide tube of the same type as the first named guide tube mounted in the passage of the elongate probe member alongside the first named guide tube and an additional needle electrode and insulation means of the same type as the first named needle electrode and insulation means disposed in the lumen of the additional guide tube and wherein the second actuator means is secured to the additional needle electrode and the additional insulation means and wherein the first actuator means causes bending of the distal extremity of the additional guide tube.

7. A device as in claim 6 wherein the second actuator means causes the first named needle electrode and insulation means to be advanced and retracted singly or together with the additional needle electrode and insulation means.

8. A device as in claim 1 wherein the actuation element is movable in the stroke from the third position to a fourth position in which the needle electrode is partially retracted relative to the guide tube so as to extend from the guide tube a predetermined distance.

9. A device as in claim 8 further comprising adjustable stop means carried by the handle means and engagable by the actuation element to selectively predetermine the fourth position and thus the distance which the needle electrode extends from the guide tube.

10. In a transurethral needle ablation device for the treatment of the prostate of a human male using radio frequency energy from a radio frequency power source, the human male having a bladder with a base, a prostate and a penis with a urethra therein formed by a urethral wall extending from the base of the bladder through the prostate and the penis along a longitudinal axis with the prostate having tissue surrounding the urethral wall near the base of the bladder, an elongate probe member having proximal and distal extremities and having a passageway extending from the proximal extremity to the distal extremity, a radio frequency conductive electrode slidably mounted in the passageway of the elongate probe and having proximal and distal extremities, an insulating sleeve longitudinally disposed on the radio frequency conductive electrode for slidable movement thereon, handle means adapted to be gripped by the human hand coupled to the proximal extremity of the elongate probe member, connector means connected to the radio frequency conductive electrode and adapted to be coupled to the radio frequency power source for supplying radio frequency energy to the radio frequency conductive electrode, a finger actuatable element mounted on the handle means and adapted to be grasped by a finger of the hand gripping the handle means, the finger actuatable element being movable in one direction from a first position to a second position and to a third position and actuation means coupled to the finger actuatable element and to the radio frequency conductive electrode and the insulating sleeve for extending the radio frequency conductive electrode and the insulating sleeve from the elongate probe member into the tissue of the prostate when the finger actuatable element is moved in the one direction from the first position to the second position and for partially retracting the insulating sleeve relative to the radio frequency conductive electrode when the finger actuatable element is moved in the one direction from the second position to the third position.

11. A device as in claim 10 in combination with the radio frequency power source and a radio frequency return for supplying radio frequency energy to the radio frequency conductive electrode to create lesions in the tissue of the prostate.

12. A device as in claim 10 further comprising guide means carried by the distal extremity of the elongate probe member and cooperatively coupled into the passageway for directing the radio frequency conductive electrode and the insulating sleeve sidewise of the longitudinal axis.

13. A device as in claim 10 wherein the actuation element is a finger lever.

14. In a transurethral needle ablation device for use by a human hand to treat the prostate of a human male using radio frequency energy from a radio frequency power source, the human male having a bladder with a base, a prostate and a penis with a urethra therein formed by a urethral wall extending from the base of the bladder through the prostate and the penis along a longitudinal axis with the prostate having tissue surrounding the urethral wall near the base of the bladder, an elongate probe member having proximal and distal extremities and having a passageway extending from the proximal extremity to the distal extremity, a guide tube mounted in the passageway of the elongate probe member and having proximal and distal extremities and a lumen extending from the proximal extremity to the distal extremity, the distal extremity of the guide tube being bent at an angle to the longitudinal axis so that the lumen in the guide tube faces the urethral wall, a needle electrode slidably mounted in the lumen of the guide tube and having proximal and distal extremities, insulation means longitudinally disposed on the needle electrode but exposing at least a portion of the distal extremity, handle means adapted to be gripped by the human hand coupled to the proximal extremity of the elongate probe member, connector means coupled to the needle electrode and adapted to be coupled to the radio frequency power source for supplying radio frequency energy to the needle electrode, a finger actuatable element mounted on the handle means and adapted to be grasped by a finger of the hand gripping the handle means, the finger actuatable element being movable in one direction from a first position to a second position and to a third position and means coupled to the finger actuatable element and to the needle electrode and the insulation means for extending the needle electrode and the insulation means from the guide tube into the tissue of the prostate when the finger actuatable element is moved from the first position to the second position and for partially retracting the insulation means relative to the needle electrode when the finger actuatable element is moved from the second position to the third position.

15. A device as in claim 14 in combination with the radio frequency power source and a radio frequency return for supplying radio frequency energy to the needle electrode to create lesions in the tissue of the prostate.

16. A device as in claim 14 wherein the finger actuatable element is movable to a fourth position, the means coupled to the finger actuatable element and to the needle electrode causing the needle electrode to retract partially relative to the guide tube when the finger actuatable element is moved to the fourth position.

17. A device as in claim 14 wherein the means coupled to the finger actuatable element and to the needle electrode and the insulation means includes first, second and third plate members disposed in juxtaposition within the handle means, the first plate member connected to the finger actuatable element and pivotable about a first axis, the second and third plate members respectively connected to the needle electrode and the insulation means and pivotable about a second axis, interengaging pin and slot means carried by the plate members for directing the movement of the second and third plate members about the second axis in response to movement of the first plate member about the first axis.

* * * * *